United States Patent
Reiser et al.

(10) Patent No.: US 10,851,356 B2
(45) Date of Patent: *Dec. 1, 2020

(54) METHOD FOR MODIFYING CHARACTERISTICS OF A LIPASE

(71) Applicant: NOVOZYMES A/S, Bagsvaerd (DK)

(72) Inventors: Anna Verena Reiser, Copenhagen (DK); Vikram Kjoeller Bhatia, Charlottelund (DK); Kim Borch, Birkerod (DK); Christian I. Joergensen, Bagsvaerd (DK); Birgitte Andersen, Bagsvaerd (DK); Lone Baunsgaard, Helsingor (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/267,525

(22) Filed: Feb. 5, 2019

(65) Prior Publication Data

US 2019/0153410 A1 May 23, 2019

Related U.S. Application Data

(62) Division of application No. 15/310,159, filed as application No. PCT/EP2015/061507 on May 26, 2015, now Pat. No. 10,221,404.

(30) Foreign Application Priority Data

May 27, 2014 (IN) .......................... 2612/CHE/2014

(51) Int. Cl.
  *C12N 9/20* (2006.01)
  *C11D 3/386* (2006.01)
  *C12N 9/50* (2006.01)
  *C12N 9/62* (2006.01)

(52) U.S. Cl.
  CPC ............... *C12N 9/20* (2013.01); *C11D 3/386* (2013.01); *C11D 3/38627* (2013.01); *C11D 3/38681* (2013.01); *C12N 9/62* (2013.01); *C12Y 301/01003* (2013.01); *C12Y 304/21064* (2013.01)

(58) Field of Classification Search
  None
  See application file for complete search history.

(56) References Cited

U.S. PATENT DOCUMENTS

| | | | | | |
|---|---|---|---|---|---|
| 6,495,357 | B1 * | 12/2002 | Fuglsang | ........... | C11D 3/38627 435/195 |
| 7,157,262 | B2 * | 1/2007 | Fuglsang | ........... | C11D 3/38627 435/196 |

FOREIGN PATENT DOCUMENTS

| | | |
|---|---|---|
| CN | 102337253 A | 2/2012 |
| CN | 103387966 A | 11/2013 |
| WO | 2004/029084 A2 | 4/2004 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Boel et al, 1988, Lipids, vol. 23, pp. 701-706.
Lui et al, 2014, Curr Microbiol, vol. 68, pp. 186-191.
Wang et al, 2012, Appl Microbiol Biotechnol, vol. 96, pp. 443-450.
Takahashi et al, 2001, Appl Microbiol Biotech 55, 454-462.
Boel et al, 1991, Uniprot access No. P19515.
Chica et al, 2005, Curr Opi Biotechnol 16, 378-384.
Singh et al, 2017, Current Protein and Peptide Science 18, 1-11.
CN 102851263—Access No. BAP47573 (Aug. 2013).
Zhu, 2013, Living chemicals and health, vol. 1, p. 148.

* cited by examiner

*Primary Examiner* — Christian L Fronda
(74) *Attorney, Agent, or Firm* — Elias Lambiris

(57) ABSTRACT

The present invention relates to a method for modifying one or more characteristics of a lipase, comprising the step of associating a peptide to the lipase, wherein the peptide has at least 50% sequence identity with the amino acid sequence of at least one major lipase contact zone of the propeptide of said lipase.

10 Claims, 1 Drawing Sheet
Specification includes a Sequence Listing.

```
SEQ ID NO: 2    ...MVLKQRA NYLGFLIVFF TAFLVEAVPI KRQSN..... .....STVDS
SEQ ID NO: 6    MVSFVSISQG ISLFFIVSSM LAGPAHAAPA SSSHSSHKNA TSSDVSTTFT
SEQ ID NO: 7    MVSFISISQG VSLCLLVSSM MLG.SSAVPV AGHKGSVKAT N....GTDFQ
SEQ ID NO: 8    MVSFISISQG VSLCLLVSSM MLG.SSAVPV SGKSGSSNTA VSA..SDNAA

SEQ ID NO: 2    LPPLIPSRTS APSSSPSTTD PEAPAM.... ......SRNG PLP....SDV
SEQ ID NO: 6    LPPIISSRVT PPKVP..SGN HNVEDDNVAK NKKWFEAHGG KLN.VTKRAD
SEQ ID NO: 7    LPPLISSRCT PPSHPETTGD PDAEAYYINK SVQWYQAHGG NYTALIKRDT
SEQ ID NO: 8    LPPLISSRCA PPSNKGSKSD LQAEPYNMQK NTEWYESHGG NLTSIGKRDD

SEQ ID NO: 2    ETKYGMALNA TSYPDSVVQA MSID.....G GIRAATSQEI NELTYYTTLS
SEQ ID NO: 6    ETVGGYTMDL PSNAPPLPAV PSTST..... .VVIASTAQI SEFKKYAGIA
SEQ ID NO: 7    ETVGGMTLDL PENPPPIPAT STAPS.SDSG EVVTATAAQI KELTNYAGVA
SEQ ID NO: 8    NLVGGMTLDL PSDAPPISLS SSTNSASDGG KVVAATTAQI QEFTKYAGIA

SEQ ID NO: 2    ANSYCRTVIP GATWDCIHC. DATEDLKIIK TWSTLIYDTN AMVARGDSEK
SEQ ID NO: 6    STAYCRSVVP LNQWSCTNCL KFVPDGKLIK TFTSLITDTN GFVLRSDAQK
SEQ ID NO: 7    ATAYCRSVVP GTKWDCKQCL KYVPDGKLIK TFTSLLTDTN GFILRSDAQK
SEQ ID NO: 8    ATAYCRSVVP GNKWDCVQCQ KWVPDGKIIT TFTSLLSDTN GYVLRSDKQK

SEQ ID NO: 2    TIYIVFRGSS SIRNWIADLT FVPVSYPPVS GTKVHKGFLD SYGEVQNELV
SEQ ID NO: 6    TIYVVFRGTN SIRSAITDLV FDLTNYTPVS GAKVHTGFYA SYKAVISDYF
SEQ ID NO: 7    TIYVTFRGTN SFRSAITDMV FTFTDYSPVK GAKVHAGFLS SYNQVVKDYF
SEQ ID NO: 8    TIYLVFRGTN SFRSAITDIV FNFSDYKPVK GAKVHAGFLS SYEQVVNDYF

SEQ ID NO: 2    ATVLDQFKQY PSYKVAVTGH SLGGATALLC ALDLYQREEG LSSSNLFLYT
SEQ ID NO: 6    PAVQSQLTAY PGYKVIVTGH SLGGAQALLA GMDLYQREPR LSKSNLAIYT
SEQ ID NO: 7    PVVQDQLTAY PDYKVIVTGH SLGGAQALLA GMDLYQREKR LSPKNLSIYT
SEQ ID NO: 8    PVVQEQLTAH PTYKVIVTGH SLGGAQALLA GMDLYQREPR LSPKNLSIFT

SEQ ID NO: 2    QGQPRVGDPA FANYVVSTGI PYRRTVNERD IVPHLPPAAF GFLHAGEEYW
SEQ ID NO: 6    VGCPRVGNPA FAYYVDSTGI TFSRSVNNRD IVPHVPPQAW GFLHPGVEAW
SEQ ID NO: 7    VGCPRVGNNA FAYYVDSTGI PFHRTVHKRD IVPHVPPQAF GYLHPGVESW
SEQ ID NO: 8    VGGPRVGNPT FAYYVESTGI PFQRTVHKRD IVPHVPPQSF GFLHPGVESW

SEQ ID NO: 2    ITDNSPETVQ VCTSDLETSD CSNSIVPFTS VLDHLSYFGI NTGLCT
SEQ ID NO: 6    ARS..SSKVQ ICTPNIETGL CSNSIVPFTS FTDHLTYYDI NEGLCL
SEQ ID NO: 7    IKED.PADVQ ICTSNIETKQ CSNSIVPFTS IADHLTYFGI NEGSCL
SEQ ID NO: 8    IKSG.TSNVQ ICTSEIETKD CSNSIVPFTS ILDHLSYFDI NEGSCL
```

METHOD FOR MODIFYING CHARACTERISTICS OF A LIPASE

CROSS-REFERENCE TO RELATED APPLICATIONS

This application is a divisional of U.S. application Ser. No. 15/310,159 filed Nov. 10, 2016, now allowed, which is a 35 U.S.C. 371 national application of PCT/EP2015/061507 filed May 26, 2015 which claims priority or the benefit under 35 U.S.C. 119 of Indian application no. 2612/CHE/2014 filed May 27, 2014, the contents of which are fully incorporated herein by reference.

REFERENCE TO SEQUENCE LISTING

This application contains a sequence listing in computer readable form. The computer readable form is incorporated herein by reference.

FIELD OF THE INVENTION

The present invention relates to lipases and methods of modifying and using them.

BACKGROUND OF THE INVENTION

Lipases are lipolytic enzymes well known as ingredient in compositions used for cleaning, fabric care and/or other treatments. Suitable compositions are continuously being developed to meet the complex requirements for efficient stain removal, low energy consumption and sustainability. Current compositions comprise many ingredients which create a harsh environment in which it is difficult for the lipases to remain active. Thus, there is a need for identifying suitable methods for modifying lipases resulting in lipases that remain active in these harsh environments.

SUMMARY OF THE INVENTION

Lipases have for many years been employed with success in various applications. However the selection of efficient lipases available for use in cleaning compositions is still quite limited. Attempts have been made to modify lipases to obtain variants with altered characteristics such as activity, stability, etc. to provide lipases with better compatibility with cleaning composition components. So far there is still a challenge in providing lipases which are not only able to survive the harsh environment of the cleaning compositions but at the same time show a wash performance.

The present invention relates to methods for generating preparation of lipases with increased stability which upon contact with detergent and/or protease may be activated or reactivated thereby providing a wash effect.

BRIEF DESCRIPTION OF THE FIGURES

FIG. 1 shows alignment of the lipase sequences SEQ ID No: 2, 6, 7, and 8.

DETAILED DISCLOSURE OF THE INVENTION

Definition

Lipase: The terms "lipase", "lipase enzyme", "lipolytic enzyme", "lipid esterase", "lipolytic polypeptide", and "lipolytic protein" refers to an enzyme in class EC3.1.1 as defined by Enzyme Nomenclature. It may have lipase activity (triacylglycerol lipase, EC3.1.1.3), cutinase activity (EC3.1.1.74), sterol esterase activity (EC3.1.1.13) and/or wax-ester hydrolase activity (EC3.1.1.50). For purposes of the present invention, lipase activity is determined according to the procedure described in the Examples, such as example 2 describing the hydrolytic activity on pNp substrates. In one aspect, the lipase of the present invention have at least 20%, e.g., at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% of the lipase activity of the polypeptide of SEQ ID NO: 3.

Lipase substrate: The term "lipase substrate" may be any substrate that is subject to the activity of a lipase as defined above.

Fabric: The term "fabric" as used herein refers to any suitable fabric, textile and/or linen serving the purpose of the present invention as described.

Wash performance: In the present context the term "wash performance" is used as an enzyme's ability to degrade and/or remove lipid or lipid-containing stains present on a fabric to be cleaned. The wash performance may be quantified by calculating the delta remission index value defined in the Methods section below. The wash performance may be measured on all types of suitable fabrics as described including any fabrics used in laundry, and industrial and institutional cleaning.

Coding sequence: The term "coding sequence" means a polynucleotide, which directly specifies the amino acid sequence of a lipase. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a lipase of the present invention. Each control sequence may be native (i.e., from the same gene) or foreign (i.e., from a different gene) to the polynucleotide encoding the lipase or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a lipase.

Expression: The term "expression" includes any step involved in the production of a lipase including, but not limited to, transcription, post-transcriptional modification, translation, post-translational modification, and secretion.

Expression vector: The term "expression vector" means a linear or circular DNA molecule that comprises a polynucleotide encoding a lipase and is operably linked to control sequences that provide for its expression.

Fragment: The term "fragment" means a polypeptide having one or more (e.g., several) amino acids absent from the amino and/or carboxyl terminus of a mature polypeptide; wherein the fragment has lipase activity. In one aspect, a fragment contains at least 50%, at least 55%, at least 60%, at least 65%, at least 70%, at least 75%, at least 80%, at least 85%, at least 90%, or at least 95% but less than 100% of the number of amino acids 1 to 269 of SEQ ID NO: 3.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to: Stability such as e.g. thermostability, thermostability in detergent, stability in detergent; Activity such as e.g. hydrolytic activity, hydrolytic activity in detergent; Substrate specific activity; Stain removal such as e.g. lipid stain removal; and Wash performance.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 269 of SEQ ID NO: 2 which is identical with amino acids 1 to 269 of SEQ ID NO: 3.

Mature polypeptide coding sequence: The term "mature polypeptide coding sequence" means a polynucleotide that encodes a mature polypeptide having lipase activity. In one aspect, the mature polypeptide coding sequence is nucleotides 292 to 1098 of SEQ ID NO: 1.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

For the purpose of the present invention other lipases should be aligned with the lipases shown in FIG. 1. The multiple alignments shown in FIG. 1 were generated by using the program Muscle v3.8.31 (http://www.drive5.com/muscle, Edgar, R. C. Nucleic Acids Res 32(5), 1792-97) which should also be used for alignment of other lipases.
Muscle v3.8.31 Basic usage
  muscle -in <inputfile>-out <outputfile>
Common options (for a complete list please see the User Guide):
  -in <inputfile> Input file in FASTA format (default stdin)
  -out <outputfile> Output alignment in FASTA format (default stdout)
  -diags Find diagonals (faster for similar sequences)
  -maxiters <n> Maximum number of iterations (integer, default 16)
  -maxhours <h> Maximum time to iterate in hours (default no limit)
  -html Write output in HTML format (default FASTA)
  -msf Write output in GCG MSF format (default FASTA)
  -clw Write output in CLUSTALW format (default FASTA)
  -clwstrict As -clw, with 'CLUSTAL W (1.81)' header
  -log[a] <logfile> Log to file (append if -loga, overwrite if -log)
  -quiet Do not write progress messages to stderr
  -version Display version information and exit
Without refinement (very fast, avg accuracy similar to T-Coffee): -maxiters 2
Fastest possible (amino acids): -maxiters 1 -diags -sv -distance1 kbit20_3
Fastest possible (nucleotides): -maxiters 1 -diags Subsequence: The term "subsequence" means a polynucleotide having one or more (e.g., several) nucleotides absent from the 5' and/or 3' end of a mature polypeptide coding sequence; wherein the subsequence encodes a fragment having lipase activity. In one aspect, a subsequence contains at least 50%, at least 55%, at least 60%, at least 65%, at least 70%, at least 75%, at least 80%, at least 85%, at least 90%, or at least 95% but less than 100% of the number of nucleotides 292 to 1098 of SEQ ID NO: 1.
Methods and Use The present invention relates to a method for modifying one or more characteristics of a lipase, comprising the step of associating a peptide to the lipase, wherein the peptide has at least 50% sequence identity with the amino acid sequence of at least one major lipase contact zone of the propeptide of said lipase.

For the purpose of calculating the sequence identity the alignment of lipases shown in FIG. 1 should be used. FIG. 1 should form basis for alignment of other lipases not shown in FIG. 1 using the procedure described in the definition of sequence identity supra.

A peptide/propeptide is associated with the mature protein of the lipase during protein synthesis and the amino acids of the peptide/propeptide may be divided into several lipase contact zones where three major lipase contact zones and four secondary lipase contact zones may be identified. The major lipase contact zones correspond to residues −57 to −46, −38 to −26, and −22 to −8 of SEQ ID NO: 2 and the four secondary lipase contact zones correspond to residues −70 to −58, −45 to −39, −25 to −23, and −7 to −1 of SEQ ID NO: 2.

In some aspects the present invention relates to a method, wherein the sequence identity with the amino acid sequence of at least one major lipase contact zone of the propeptide of said lipase is at least 55%; at least 60%; at least 65%; at least 70%; at least 75%; at least 80%; at least 85%; at least 90%; at least 91%; least 92%; least 93%; least 94%; least 95%; least 96%; least 97%; least 98%; least 99%; or 100% of SEQ ID NO: 2.

In some aspects the present invention relates to a method, wherein the lipase has at least 75%, at least 80%, at least 85%, at least 90%, at least 95%, at least 96%, at least 97%, at least 98%, at least 99%; or 100% sequence identity with amino acid 1 to 269 of SEQ ID NO: 2.

It should be understood that specific variants disclosed in the two co-filed patent applications relating to lipase variants (12937) and lipase propeptide variants (12960) respectively which are hereby incorporated by reference may also be used in the methods for modifying a lipase as described in the present invention.

The inventors have found that a propeptide may be isolated from the N-terminus of RmL is able to bind to said lipase. They have shown that the propeptide of RmL has lipase inhibitory activity. It is thus suggested that N-terminal propeptides isolated from any suitable lipase may be used for inhibiting lipase activity. In some aspects the present invention relates to use of the propeptide for inhibiting the enzymatic activity of a lipase upon binding of the propeptide to said lipase. The activity may be hydrolytic activity, substrate specific activity and/or any other activity.

The inventors have furthermore shown that the propeptide increases the stability of the lipase. It is thus suggested that N-terminal propeptides isolated from any suitable lipase may be used for increasing stability of a lipase. In some aspects the present invention relates to use of the propeptide for increasing stability of a lipase upon binding of the propeptide to said lipase.

The stability may be thermostability, thermostability in detergent, stability in detergent, stability during storage and/or any other stability The inventors have demonstrated that the propeptide decreases wash performance of the lipase. It is thus suggested that N-terminal propeptides isolated from any suitable lipase may be used for decreasing wash performance of a lipase. In some aspects the present invention relates to use of the propeptide for decreasing wash performance of a lipase upon binding of the propeptide to said lipase.

The inventors have also found that the propeptide decreases lipid stain removal of the lipase. It is thus suggested that N-terminal propeptides isolated from any suitable lipase may be used for decreasing lipid stain removal of a lipase. In some aspects the present invention relates to use of the propeptide for decreasing lipid stain removal of a lipase upon binding of the propeptide to said lipase.

In some aspects the present invention relates to a method, wherein the characteristics are selected from: Stability such as thermostability, stability in detergent and/or stability during storage; Activity such as substrate specific activity and/or hydrolytic activity; Lipid stain removal; and Wash performance.

In some aspects the present invention relates to a method, wherein the modified characteristic is selected from: Increased stability; Decreased activity; Decreased lipid stain removal, and Decreased wash performance.

Assays suitable for determining activity such as substrate specific activity and/or hydrolytic activity may be e.g. the p-Nitrophenyl (pNp) acyl ester assay as described in example 2. Assays suitable for determining stability may be e.g. the Differential Scanning calorimetry (DSC) assay as described in example 3. Assays suitable for determining lipid stain removal and/or wash performance may be e.g. the Automated Mechanical Stress Assay (AMSA) as described in example 4.

In some aspects the present invention relates to a modified lipase prepared according to the method.

Polynucleotides

The present invention also relates to polynucleotides encoding a polypeptide used to a modified lipase.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Applications*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Rhizomucor miehei* or a related organism and thus, for example, may be an allelic or species variant of the polypeptide encoding region of the polynucleotide.

Modification of a polynucleotide encoding a polypeptide for the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide encoding a lipase of the present invention operably linked to one or more control sequences that direct the expression of the coding sequence in a suitable host cell under conditions compatible with the control sequences.

The polynucleotide may be manipulated in a variety of ways to provide for expression of a lipase. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the lipase. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO96/00787), *Fusarium venenatum* amyloglucosidase (WO00/56900), *Fusarium venenatum* Daria (WO00/56900), *Fusarium venenatum* Quinn (WO00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the lipase. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the lipase. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the lipase-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a lipase and directs the lipase into the cell's secretory pathway. The 5'-end of the coding sequence of the polynucleotide may inherently contain a signal peptide coding sequence naturally linked in translation reading frame with the segment of the coding sequence that encodes the lipase. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the lipase. However, any signal peptide coding sequence that directs the expressed lipase into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a lipase. Where both signal peptide and propeptide sequences are present, the propeptide sequence is positioned next to the N-terminus of the lipase and the signal peptide sequence is positioned next to the N-terminus of the propeptide sequence.

It may also be desirable to add regulatory sequences that regulate expression of the lipase relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the lipase would be operably linked with the regulatory sequence.

Expression Vectors

The present invention also relates to recombinant expression vectors comprising a polynucleotide encoding a lipase of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the lipase at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the lipase or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a lipase. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a lipase of the present invention operably linked to one or more control sequences that direct the production of a lipase of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the lipase and its source.

The host cell may be any cell useful in the recombinant production of a lipase, e.g., a prokaryote or a eukaryote.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell, including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. MicrobioL Methods* 64: 391-397), or conjugation (see, e.g., Pinedo and Smets, 2005, *Appl. Environ. MicrobioL* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida*, *Hansenula*, *Kluyveromyces*, *Pichia*, *Saccharomyces*, *Schizosaccharomyces*, or *Yarrowia* cell such as a *Kluyveromyces lactis*, *Saccharomyces carisbergensis*, *Saccharomyces cerevisiae*, *Saccharomyces diastaticus*, *Saccharomyces douglasii*,

*Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Detergents

In some aspects the present invention relates to a composition comprising the lipase prepared according to the method.

In some aspects the present invention relates to a composition formulated as a regular, compact or concentrated liquid; a gel; a paste; a soap bar; a regular or a compacted powder; a granulated solid; a homogenous or a multilayer tablet with two or more layers (same or different phases); a pouch having one or more compartments; a single or a multi-compartment unit dose form; or any combination thereof.

In some aspects the present invention relates to a composition further comprising protease and/or detergent.

In some aspects the present invention relates to a method for increasing the activity of the modified lipase, comprising a step of bringing said modified lipase into contact with protease and/or detergent.

The non-limiting list of detergent composition components illustrated hereinafter are suitable for use in the detergent compositions and methods herein may be desirably incorporated in certain embodiments of the invention, e.g. to assist or enhance cleaning performance, for treatment of the substrate to be cleaned, or to modify the aesthetics of the composition as is the case with perfumes, colorants, dyes or the like. The levels of any such components incorporated in any compositions are in addition to any materials previously recited for incorporation. The precise nature of these additional components, and levels of incorporation thereof, will depend on the physical form of the composition and the nature of the cleaning operation for which it is to be used. Although components mentioned below are categorized by general header according to a particular functionality, this is not to be construed as a limitation, as a component may comprise additional functionalities as will be appreciated by the skilled artisan.

Unless otherwise indicated the amounts in percentage is by weight of the composition (wt %). Suitable component materials include, but are not limited to, surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, fabric softeners, carriers, hydrotropes, processing aids, solvents and/or pigments. In addition to the disclosure below, suitable examples of such other components and levels of use are found in U.S. Pat. Nos. 5,576,282, 6,306,812, and 6,326,348 hereby incorporated by reference.

Thus, in certain embodiments the invention do not contain one or more of the following adjuncts materials: surfactants, soaps, builders, chelating agents, dye transfer inhibiting agents, dispersants, additional enzymes, enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, perfume delivery systems, structure elasticizing agents, fabric softeners, carriers, hydrotropes, processing aids, solvents and/or pigments. However, when one or more components are present, such one or more components may be present as detailed below:

Surfactants—The compositions according to the present invention may comprise a surfactant or surfactant system wherein the surfactant can be selected from nonionic surfactants, anionic surfactants, cationic surfactants, ampholytic surfactants, zwitterionic surfactants, semi-polar non-ionic surfactants and mixtures thereof. When present, surfactant is typically present at a level of from 0.1 to 60 wt %, from 0.2 to 40 wt %, from 0.5 to 30 wt %, from 1 to 50 wt %, from 1 to 40 wt %, from 1 to 30 wt %, from 1 to 20 wt %, from 3 to 10 wt %, from 3 to 5 wt %, from 5 to 40 wt %, from 5 to 30 wt %, from 5 to 15 wt %, from 3 to 20 wt %, from 3 to 10 wt %, from 8 to 12 wt %, from 10 to 12 wt % or from 20 to 25 wt %.

Suitable anionic detersive surfactants include sulphate and sulphonate detersive surfactants.

Suitable sulphonate detersive surfactants include alkyl benzene sulphonate, in one aspect, $C_{10-13}$ alkyl benzene sulphonate. Suitable alkyl benzene sulphonate (LAS) may be obtained, by sulphonating commercially available linear alkyl benzene (LAB); suitable LAB includes low 2-phenyl LAB, such as Isochem® or Petrelab®, other suitable LAB include high 2-phenyl LAB, such as Hyblene®. A suitable anionic detersive surfactant is alkyl benzene sulphonate that is obtained by DETAL catalyzed process, although other synthesis routes, such as HF, may also be suitable. In one aspect a magnesium salt of LAS is used.

Suitable sulphate detersive surfactants include alkyl sulphate, in one aspect, $C_{8-18}$ alkyl sulphate, or predominantly $C_{12}$ alkyl sulphate.

Another suitable sulphate detersive surfactant is alkyl alkoxylated sulphate, in one aspect, alkyl ethoxylated sulphate, in one aspect, a $C_{8-18}$ alkyl alkoxylated sulphate, in another aspect, a $C_{8-18}$ alkyl ethoxylated sulphate, typically the alkyl alkoxylated sulphate has an average degree of alkoxylation of from 0.5 to 20, or from 0.5 to 10, typically the alkyl alkoxylated sulphate is a $C_{8-18}$ alkyl ethoxylated sulphate having an average degree of ethoxylation of from 0.5 to 10, from 0.5 to 7, from 0.5 to 5 or from 0.5 to 3.

The alkyl sulphate, alkyl alkoxylated sulphate and alkyl benzene sulphonates may be linear or branched, substituted or un-substituted.

The detersive surfactant may be a mid-chain branched detersive surfactant, in one aspect, a mid-chain branched anionic detersive surfactant, in one aspect, a mid-chain branched alkyl sulphate and/or a mid-chain branched alkyl benzene sulphonate, e.g. a mid-chain branched alkyl sulphate. In one aspect, the mid-chain branches are $C_{1-4}$ alkyl groups, typically methyl and/or ethyl groups.

Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

Suitable non-ionic detersive surfactants are selected from the group consisting of: $C_8$-$C_{18}$ alkyl ethoxylates, such as, NEODOL®; $C_6$-$C_{12}$ alkyl phenol alkoxylates wherein the alkoxylate units may be ethyleneoxy units, propyleneoxy units or a mixture thereof; $C_{12}$-$C_{18}$ alcohol and $C_6$-$C_{12}$ alkyl phenol condensates with ethylene oxide/propylene oxide block polymers such as Pluronic®; $C_{14}$-$C_{22}$ mid-chain branched alcohols; $C_{14}$-$C_{22}$ mid-chain branched alkyl alkoxylates, typically having an average degree of alkoxylation of from 1 to 30; alkylpolysaccharides, in one aspect, alkylpolyglycosides; polyhydroxy fatty acid amides; ether capped poly(oxyalkylated) alcohol surfactants; and mixtures thereof.

Suitable non-ionic detersive surfactants include alkyl polyglucoside and/or an alkyl alkoxylated alcohol.

In one aspect, non-ionic detersive surfactants include alkyl alkoxylated alcohols, in one aspect $C_{8-18}$ alkyl alkoxylated alcohol, e.g. a $C_{8-18}$ alkyl ethoxylated alcohol, the alkyl alkoxylated alcohol may have an average degree of alkoxylation of from 1 to 50, from 1 to 30, from 1 to 20, or from 1 to 10. In one aspect, the alkyl alkoxylated alcohol may be a $C_{8-18}$ alkyl ethoxylated alcohol having an average degree of ethoxylation of from 1 to 10, from 1 to 7, more from 1 to 5 or from 3 to 7. The alkyl alkoxylated alcohol can be linear or branched, and substituted or un-substituted. Suitable nonionic surfactants include Lutensol®.

Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

Suitable cationic detersive surfactants include alkyl pyridinium compounds, alkyl quaternary ammonium compounds, alkyl quaternary phosphonium compounds, alkyl ternary sulphonium compounds, and mixtures thereof.

Suitable cationic detersive surfactants are quaternary ammonium compounds having the general formula: $(R)(R_1)(R_2)(R_3)N^+\ X^-$, wherein R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, suitable anions include: halides, e.g. chloride; sulphate; and sulphonate. Suitable cationic detersive surfactants are mono-$C_{6-18}$ alkyl mono-hydroxyethyl di-methyl quaternary ammonium chlorides. Highly suitable cationic detersive surfactants are mono-$C_{8-10}$ alkyl mono-hydroxyethyl di-methyl quaternary ammonium chloride, mono-$C_{10-12}$ alkyl mono-hydroxyethyl di-methyl quaternary ammonium chloride and mono-$C_{10}$ alkyl mono-hydroxyethyl di-methyl quaternary ammonium chloride.

Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

Suitable amphoteric/zwitterionic surfactants include amine oxides and betaines such as alkyldimethylbetaines, sulfobetaines, or combinations thereof. Amine-neutralized anionic surfactants—Anionic surfactants of the present invention and adjunct anionic cosurfactants, may exist in an acid form, and said acid form may be neutralized to form a surfactant salt which is desirable for use in the present detergent compositions. Typical agents for neutralization include the metal counterion base such as hydroxides, eg, NaOH or KOH. Further preferred agents for neutralizing anionic surfactants of the present invention and adjunct anionic surfactants or cosurfactants in their acid forms include ammonia, amines, or alkanolamines. Alkanolamines are preferred. Suitable non-limiting examples including monoethanolamine, diethanolamine, triethanolamine, and other linear or branched alkanolamines known in the art; e.g., highly preferred alkanolamines include 2-amino-1-propanol, 1-aminopropanol, monoisopropanolamine, or 1-amino-3-propanol. Amine neutralization may be done to a full or partial extent, e.g. part of the anionic surfactant mix may be neutralized with sodium or potassium and part of the anionic surfactant mix may be neutralized with amines or alkanolamines.

Non-limiting examples of semipolar surfactants include amine oxides (AO) such as alkyldimethylamineoxide Surfactant systems comprising mixtures of one or more anionic and in addition one or more nonionic surfactants optionally with an additional surfactant such as a cationic surfactant, may be preferred. Preferred weight ratios of anionic to nonionic surfactant are at least 2:1, or at least 1:1 to 1:10.

Soap—The compositions herein may contain soap. Without being limited by theory, it may be desirable to include soap as it acts in part as a surfactant and in part as a builder and may be useful for suppression of foam and may furthermore interact favorably with the various cationic compounds of the composition to enhance softness on textile fabrics treaded with the inventive compositions. Any soap known in the art for use in laundry detergents may be utilized. In one embodiment, the compositions contain from 0 wt % to 20 wt %, from 0.5 wt % to 20 wt %, from 4 wt % to 10 wt %, or from 4 wt % to 7 wt % of soap.

Examples of soap useful herein include oleic acid soaps, palmitic acid soaps, palm kernel fatty acid soaps, and mixtures thereof. Typical soaps are in the form of mixtures of fatty acid soaps having different chain lengths and degrees of substitution. One such mixture is topped palm kernel fatty acid.

In one embodiment, the soap is selected from free fatty acid. Suitable fatty acids are saturated and/or unsaturated and can be obtained from natural sources such a plant or animal esters (e.g., palm kernel oil, palm oil, coconut oil, babassu oil, safflower oil, tall oil, castor oil, tallow and fish oils, grease, and mixtures thereof), or synthetically prepared (e.g., via the oxidation of petroleum or by hydrogenation of carbon monoxide via the Fisher Tropsch process).

Examples of suitable saturated fatty acids for use in the compositions of this invention include capric, lauric, myristic, palmitic, stearic, arachidic and behenic acid. Suitable unsaturated fatty acid species include: palmitoleic, oleic, linoleic, linolenic and ricinoleic acid. Examples of preferred fatty acids are saturated Cn fatty acid, saturated $C_{i_2}$-$C_{i_4}$ fatty acids, and saturated or unsaturated Cn to $C_{i_8}$ fatty acids, and mixtures thereof.

When present, the weight ratio of fabric softening cationic cosurfactant to fatty acid is preferably from about 1:3 to about 3:1, more preferably from about 1:1.5 to about 1.5:1, most preferably about 1:1.

Levels of soap and of nonsoap anionic surfactants herein are percentages by weight of the detergent composition, specified on an acid form basis. However, as is commonly understood in the art, anionic surfactants and soaps are in practice neutralized using sodium, potassium or alkanolammonium bases, such as sodium hydroxide or monoethanolamine.

Hydrotropes—The compositions of the present invention may comprise one or more hydrotropes. A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain from 0 to 10 wt %, such as from 0 to 5 wt %, 0.5 to 5 wt %, or from 3% to 5 wt %, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders—The compositions of the present invention may comprise one or more builders, co-builders, builder systems or a mixture thereof. When a builder is used, the cleaning composition will typically comprise from 0 to 65 wt %, at least 1 wt %, from 2 to 60 wt % or from 5 to 10 wt % builder. In a dish wash cleaning composition, the level of builder is typically 40 to 65 wt % or 50 to 65 wt %. The composition may be substantially free of builder; substantially free means "no deliberately added" zeolite and/or phosphate. Typical zeolite builders include zeolite A, zeolite P and zeolite MAP. A typical phosphate builder is sodium tri-polyphosphate.

The builder and/or co-builder may particularly be a chelating agent that forms water-soluble complexes with Ca and Mg. Any builder and/or co-builder known in the art for use in detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), iminodiethanol (DEA) and 2,2',2"-nitrilotriethanol (TEA), and carboxymethylinulin (CMI), and combinations thereof.

The cleaning composition may include a co-builder alone, or in combination with a builder, e.g. a zeolite builder. Non-limiting examples of co-builders include homopolymers of polyacrylates or copolymers thereof, such as poly (acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), etheylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diyl-bis(phosphonic acid) (HEDP), ethylenediaminetetrakis(methylene)tetrakis(phosphonic acid) (EDTMPA), diethylenetriaminepentakis(methylene)pentakis(phosphonic acid) (DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(hydroxyethyl)-ethylidenediaminetriacetate (HEDTA), diethanolglycine (DEG), Diethylenetriamine Penta (Methylene Phosphonic acid) (DTPMP), aminotris(methylenephosphonic acid) (ATMP), and combinations and salts thereof. Further exemplary builders and/or co-builders are described in, e.g., WO09/102854, U.S. Pat. No. 5,977,053.

Chelating Agents and Crystal Growth Inhibitors—The compositions herein may contain a chelating agent and/or a crystal growth inhibitor. Suitable molecules include copper, iron and/or manganese chelating agents and mixtures thereof. Suitable molecules include DTPA (Diethylene triamine pentaacetic acid), HEDP (Hydroxyethane diphosphonic acid), DTPMP (Diethylene triamine penta(methylene phosphonic acid)), 1,2-Dihydroxybenzene-3,5-disulfonic acid disodium salt hydrate, ethylenediamine, diethylene triamine, ethylenediaminedisuccinic acid (EDDS), N-hydroxyethylethylenediaminetri-acetic acid (HEDTA), triethylenetetraaminehexaacetic acid (TTHA), N-hydroxyethyl-iminodiacetic acid (HEIDA), dihydroxyethylglycine (DHEG), ethylenediaminetetrapropionic acid (EDTP), carboxymethyl inulin and 2-Phosphonobutane 1,2,4-tricarboxylic acid (Bayhibit® AM) and derivatives thereof. Typically the composition may comprise from 0.005 to 15 wt % or from 3.0 to 10 wt % chelating agent or crystal growth inhibitor.

Bleach Component—The bleach component suitable for incorporation in the methods and compositions of the invention comprise one or a mixture of more than one bleach component. Suitable bleach components include bleaching catalysts, photobleaches, bleach activators, hydrogen peroxide, sources of hydrogen peroxide, pre-formed peracids and mixtures thereof. In general, when a bleach component is used, the compositions of the present invention may comprise from 0 to 30 wt %, from 0.00001 to 90 wt %, 0.0001 to 50 wt %, from 0.001 to 25 wt % or from 1 to 20 wt %. Examples of suitable bleach components include:

(1) Pre-formed peracids: Suitable preformed peracids include, but are not limited to, compounds selected from the group consisting of pre-formed peroxyacids or salts thereof, typically either a peroxycarboxylic acid or salt thereof, or a peroxysulphonic acid or salt thereof.

The pre-formed peroxyacid or salt thereof is preferably a peroxycarboxylic acid or salt thereof, typically having a chemical structure corresponding to the following chemical formula:

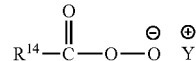

wherein: $R^{14}$ is selected from alkyl, aralkyl, cycloalkyl, aryl or heterocyclic groups; the $R^{14}$ group can be linear or branched, substituted or unsubstituted; and Y is any suitable counter-ion that achieves electric charge neutrality, preferably Y is selected from hydrogen, sodium or potassium. Preferably, $R^{14}$ is a linear or branched, substituted or unsubstituted $C_{6-9}$ alkyl. Preferably, the peroxyacid or salt thereof is selected from peroxyhexanoic acid, peroxyheptanoic acid, peroxyoctanoic acid, peroxynonanoic acid, peroxydecanoic acid, any salt thereof, or any combination thereof. Particularly preferred peroxyacids are phthalimido-peroxy-alkanoic acids, in particular ε-phthahlimido peroxy hexanoic acid (PAP). Preferably, the peroxyacid or salt thereof has a melting point in the range of from 30° C. to 60° C.

The pre-formed peroxyacid or salt thereof can also be a peroxysulphonic acid or salt thereof, typically having a chemical structure corresponding to the following chemical formula:

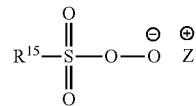

wherein: $R^{15}$ is selected from alkyl, aralkyl, cycloalkyl, aryl or heterocyclic groups; the $R^{15}$ group can be linear or branched, substituted or unsubstituted; and Z is any suitable counter-ion that achieves electric charge neutrality, preferably Z is selected from hydrogen, sodium or potassium. Preferably $R^{15}$ is a linear or branched, substituted or unsubstituted $C_{6-9}$ alkyl. Preferably such bleach components may be present in the compositions of the invention in an amount from 0.01 to 50 wt % or from 0.1 to 20 wt %.

(2) Sources of hydrogen peroxide include e.g., inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts such as those selected from the group consisting of sodium salts of perborate, percarbonate and mixtures thereof. When employed, inorganic perhydrate salts are typically present in amounts of 0.05 to 40 wt % or 1 to 30 wt % of the overall composition and are typically incorporated into such compositions as a crystalline solid that may be coated. Suitable coatings include: inorganic salts such as alkali metal silicate, carbonate or borate salts or mixtures thereof, or organic materials such as water-soluble or dispersible polymers, waxes, oils or fatty soaps. Preferably such bleach components may be present in the compositions of the invention in an amount of 0.01 to 50 wt % or 0.1 to 20 wt %.

(3) The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable bleach activators are those having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED), sodium 4-[(3,5,5-trimethylhexanoyl)oxy] benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO98/17767. A family of bleach activators is disclosed in EP624154 and particularly preferred in that family is acetyl triethyl citrate (ATC). ATC or a short chain triglyceride like triacetin has the advantage that it is environmentally friendly. Furthermore acetyl triethyl citrate and triacetin have good hydrolytical stability in the product upon storage and are efficient bleach activators. Finally ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxyhexanoic acid (PAP). Suitable bleach activators are also disclosed in WO98/17767. While any suitable bleach activator may be employed, in one aspect of the invention the subject cleaning composition may comprise NOBS, TAED or mixtures thereof. When present, the peracid and/or bleach activator is generally present in the composition in an amount of 0.1 to 60 wt %, 0.5 to 40 wt % or 0.6 to 10 wt % based on the fabric and home care composition. One or more hydrophobic peracids or precursors thereof may be used in combination with one or more hydrophilic peracid or precursor thereof. Preferably such bleach components may be present in the compositions of the invention in an amount of 0.01 to 50 wt %, or 0.1 to 20 wt %.

The amounts of hydrogen peroxide source and peracid or bleach activator may be selected such that the molar ratio of available oxygen (from the peroxide source) to peracid is from 1:1 to 35:1, or even 2:1 to 10:1.

(4) Diacyl peroxides—preferred diacyl peroxide bleaching species include those selected from diacyl peroxides of the general formula: $R^1$—C(O)—OO—(O)C—$R^2$, in which $R^1$ represents a $C_6$-$C_{18}$ alkyl, preferably $C_6$-$C_{12}$ alkyl group containing a linear chain of at least 5 carbon atoms and optionally containing one or more substituents (e.g. —$N^+$($CH_3$)$_3$, —COOH or —CN) and/or one or more interrupting moieties (e.g. —CONH— or —CH=CH—) interpolated between adjacent carbon atoms of the alkyl radical, and $R^2$ represents an aliphatic group compatible with a peroxide moiety, such that $R^1$ and $R^2$ together contain a total of 8 to 30 carbon atoms. In one preferred aspect $R^1$ and $R^2$ are linear unsubstituted $C_6$-$C_{12}$ alkyl chains. Most preferably $R^1$ and $R^2$ are identical. Diacyl peroxides, in which both $R^1$ and $R^2$ are $C_6$-$C_{12}$ alkyl groups, are particularly preferred. Preferably, at least one of, most preferably only one of, the R groups ($R_1$ or $R_2$), does not contain branching or pendant rings in the alpha position, or preferably neither in the alpha nor beta positions or most preferably in none of the alpha or beta or gamma positions. In one further preferred embodiment the DAP may be asymmetric, such that preferably the hydrolysis of R1 acyl group is rapid to generate peracid, but the hydrolysis of R2 acyl group is slow.

The tetraacyl peroxide bleaching species is preferably selected from tetraacyl peroxides of the general formula: $R^3$—C(O)—OO—C(O)—($CH_2$)n-C(O)—OO—C(O)—$R^3$, in which $R^3$ represents a $C_1$-$C_9$ alkyl, or $C_3$-$C_7$ group and n represents an integer from 2 to 12, or 4 to 10 inclusive.

Preferably, the diacyl and/or tetraacyl peroxide bleaching species is present in an amount sufficient to provide at least 0.5 ppm, at least 10 ppm, or at least 50 ppm by weight of the wash liquor. In a preferred embodiment, the bleaching species is present in an amount sufficient to provide from 0.5 to 300 ppm, from 30 to 150 ppm by weight of the wash liquor. Preferably the bleach component comprises a bleach catalyst (5 and 6).

(5) Preferred are organic (non-metal) bleach catalysts include bleach catalyst capable of accepting an oxygen atom from a peroxyacid and/or salt thereof, and transferring the oxygen atom to an oxidizeable substrate. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof.

Suitable iminium cations and polyions include, but are not limited to, N-methyl-3,4-dihydroisoquinolinium tetrafluoroborate, prepared as described in Tetrahedron (1992), 49(2), 423-38 (e.g. compound 4, p. 433); N-methyl-3,4-dihydroisoquinolinium p-toluene sulphonate, prepared as described in U.S. Pat. No. 5,360,569 (e.g. Column 11, Example 1); and N-octyl-3,4-dihydroisoquinolinium p-toluene sulphonate, prepared as described in U.S. Pat. No. 5,360,568 (e.g. Column 10, Ex. 3).

Suitable iminium zwitterions include, but are not limited to, N-(3-sulfopropyl)-3,4-dihydroisoquinolinium, inner salt, prepared as described in U.S. Pat. No. 5,576,282 (e.g. Column 31, Ex. II); N-[2-(sulphooxy)dodecyl]-3,4-dihydroisoquinolinium, inner salt, prepared as described in U.S. Pat. No. 5,817,614 (e.g. Column 32, Ex. V); 2-[3-[(2-ethylhexyl)oxy]-2-(sulphooxy)propyl]-3,4-dihydroisoquinolinium, inner salt, prepared as described in WO05/047264 (e.g. p. 18, Ex. 8), and 2-[3-[(2-butylocty)poxy]-2-(sulphooxy)propyl]-3,4-dihydroisoquinolinium, inner salt.

Suitable modified amine oxygen transfer catalysts include, but are not limited to, 1,2,3,4-tetrahydro-2-methyl-1-isoquinolinol, which can be made according to the procedures described in Tetrahedron Letters (1987), 28(48), 6061-6064. Suitable modified amine oxide oxygen transfer catalysts include, but are not limited to, sodium 1-hydroxy-N-oxy-N-[2-(sulphooxy)decyl]-1,2,3,4-tetrahydroisoquinoline.

Suitable N-sulphonyl imine oxygen transfer catalysts include, but are not limited to, 3-methyl-1,2-benzisothiazole 1,1-dioxide, prepared according to the procedure described in the Journal of Organic Chemistry (1990), 55(4), 1254-61.

Suitable N-phosphonyl imine oxygen transfer catalysts include, but are not limited to, [R-(E)]-N-[(2-chloro-5-nitrophenyl)methylene]-P-phenyl-P-(2,4,6-trimethylphenyl)-phosphinic amide, which can be made according to the procedures described in the Journal of the Chemical Society, Chemical Communications (1994), (22), 2569-70.

Suitable N-acyl imine oxygen transfer catalysts include, but are not limited to, [N(E)]-N-(phenylmethylene)acetamide, which can be made according to the procedures described in Polish Journal of Chemistry (2003), 77(5), 577-590.

Suitable thiadiazole dioxide oxygen transfer catalysts include but are not limited to, 3-methyl-4-phenyl-1,2,5-thiadiazole 1,1-dioxide, which can be made according to the procedures described in U.S. Pat. No. 5,753,599 (Column 9, Ex. 2).

Suitable perfluoroimine oxygen transfer catalysts include, but are not limited to, (Z)-2,2,3,3,4,4,4-heptafluoro-N-(non-afluorobutyl)butanimidoyl fluoride, which can be made according to the procedures described in Tetrahedron Letters (1994), 35(34), 6329-30.

Suitable cyclic sugar ketone oxygen transfer catalysts include, but are not limited to, 1,2:4,5-di-O-isopropylidene-D-erythro-2,3-hexodiuro-2,6-pyranose as prepared in U.S. Pat. No. 6,649,085 (Column 12, Ex. 1).

Preferably, the bleach catalyst comprises an iminium and/or carbonyl functional group and is typically capable of forming an oxaziridinium and/or dioxirane functional group upon acceptance of an oxygen atom, especially upon acceptance of an oxygen atom from a peroxyacid and/or salt thereof. Preferably, the bleach catalyst comprises an oxaziridinium functional group and/or is capable of forming an oxaziridinium functional group upon acceptance of an oxygen atom, especially upon acceptance of an oxygen atom from a peroxyacid and/or salt thereof. Preferably, the bleach catalyst comprises a cyclic iminium functional group, preferably wherein the cyclic moiety has a ring size of from five to eight atoms (including the nitrogen atom), preferably six atoms. Preferably, the bleach catalyst comprises an aryliminium functional group, preferably a bi-cyclic aryliminium functional group, preferably a 3,4-dihydroisoquinolinium functional group. Typically, the imine functional group is a quaternary imine functional group and is typically capable of forming a quaternary oxaziridinium functional group upon acceptance of an oxygen atom, especially upon acceptance of an oxygen atom from a peroxyacid and/or salt thereof. In another aspect, the detergent composition comprises a bleach component having a log $P_{o/w}$, no greater than 0, no greater than –0.5, no greater than –1.0, no greater than –1.5, no greater than –2.0, no greater than –2.5, no greater than –3.0, or no greater than –3.5. The method for determining log $P_{o/w}$, is described in more detail below.

Typically, the bleach ingredient is capable of generating a bleaching species having a $X_{SO}$ of from 0.01 to 0.30, from 0.05 to 0.25, or from 0.10 to 0.20. The method for determining $X_{SO}$ is described in more detail below. For example, bleaching ingredients having an isoquinolinium structure are capable of generating a bleaching species that has an oxaziridinium structure. In this example, the $X_{SO}$ is that of the oxaziridinium bleaching species.

Preferably, the bleach catalyst has a chemical structure corresponding to the following chemical formula:

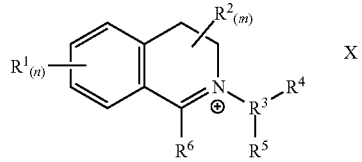

wherein: n and m are independently from 0 to 4, preferably n and m are both 0; each $R^1$ is independently selected from a substituted or unsubstituted radical selected from the group consisting of hydrogen, alkyl, cycloalkyl, aryl, fused aryl, heterocyclic ring, fused heterocyclic ring, nitro, halo, cyano, sulphonato, alkoxy, keto, carboxylic, and carboalkoxy radicals; and any two vicinal $R^1$ substituents may combine to form a fused aryl, fused carbocyclic or fused heterocyclic ring; each $R^2$ is independently selected from a substituted or unsubstituted radical independently selected from the group consisting of hydrogen, hydroxy, alkyl, cycloalkyl, alkaryl, aryl, aralkyl, alkylenes, heterocyclic ring, alkoxys, arylcarbonyl groups, carboxyalkyl groups and amide groups; any $R^2$ may be joined together with any other of $R^2$ to form part of a common ring; any geminal $R^2$ may combine to form a carbonyl; and any two $R^2$ may combine to form a substituted or unsubstituted fused unsaturated moiety; $R^3$ is a $C_1$ to $C_{20}$ substituted or unsubstituted alkyl; $R^4$ is hydrogen or the moiety $Q_t$-A, wherein: Q is a branched or unbranched alkylene, t=0 or 1 and A is an anionic group selected from the group consisting of $OSO_3^-$, $SO_3^-$, $CO_2^-$, $OCO_2^-$, $OPO_3^{2-}$, $OPO_3H^-$ and $OPO_2^-$; $R^5$ is hydrogen or the moiety —$CR^{11}R^{12}$—Y—$G_b$-$Y_c$—[$(CR^9R^{10})_y$—O]$_k$—$R^8$ wherein: each Y is independently selected from the group consisting of O, S, N—H, or N—$R^8$; and each $R^8$ is independently selected from the group consisting of alkyl, aryl and heteroaryl, said moieties being substituted or unsubstituted, and whether substituted or unsubstituted said moieties having less than 21 carbons; each G is independently selected from the group consisting of CO, $SO_2$, SO, PO and $PO_2$; $R^9$ and $R^{19}$ are independently selected from the group consisting of H and $C_1$-$C_4$ alkyl; $R^{11}$ and $R^{12}$ are independently selected from the group consisting of H and alkyl, or when taken together may join to form a carbonyl; b=0 or 1; c can=0 or 1, but c must=0 if b=0; y is an integer from 1 to 6; k is an integer from 0 to 20; $R^6$ is H, or an alkyl, aryl or heteroaryl moiety; said moieties being substituted or unsubstituted; and X, if present, is a suitable charge balancing counterion, preferably X is present when $R^4$ is hydrogen, suitable X, include but are not limited to: chloride, bromide, sulphate, methosulphate, sulphonate, p-toluenesulphonate, borontetraflouride and phosphate.

In one embodiment of the present invention, the bleach catalyst has a structure corresponding to general formula below:

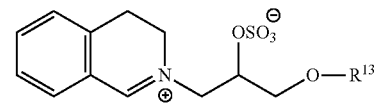

wherein $R^{13}$ is a branched alkyl group containing from three to 24 carbon atoms (including the branching carbon atoms) or a linear alkyl group containing from one to 24 carbon atoms; preferably $R^{13}$ is a branched alkyl group containing from eight to 18 carbon atoms or linear alkyl group containing from eight to eighteen carbon atoms; preferably $R^{13}$ is selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl; preferably $R^{13}$ is selected from the group consisting of 2-butyloctyl, 2-pentylnonyl, 2-hexyldecyl, iso-tridecyl and iso-pentadecyl.

Preferably the bleach component comprises a source of peracid in addition to bleach catalyst, particularly organic bleach catalyst. The source of peracid may be selected from (a) pre-formed peracid; (b) percarbonate, perborate or persulfate salt (hydrogen peroxide source) preferably in combination with a bleach activator; and (c) perhydrolase enzyme and an ester for forming peracid in situ in the presence of water in a textile or hard surface treatment step.

When present, the peracid and/or bleach activator is generally present in the composition in an amount of from 0.1 to 60 wt %, from 0.5 to 40 wt % or from 0.6 to 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or 2:1 to 10:1.

(6) Metal-containing Bleach Catalysts—The bleach component may be provided by a catalytic metal complex. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243. Preferred catalysts are described in WO09/839406, U.S. Pat. No. 6,218,351 and WO00/012667. Particularly preferred are transition metal catalyst or ligands therefore that are cross-bridged polydentate N-donor ligands.

If desired, the compositions herein can be catalyzed by means of a manganese compound. Such compounds and levels of use are well known in the art and include, e.g., the manganese-based catalysts disclosed in U.S. Pat. No. 5,576,282.

Cobalt bleach catalysts useful herein are known, and are described e.g. in U.S. Pat. Nos. 5,597,936; 5,595,967. Such cobalt catalysts are readily prepared by known procedures, such as taught e.g. in U.S. Pat. Nos. 5,597,936 and 5,595,967.

Compositions herein may also suitably include a transition metal complex of ligands such as bispidones (U.S. Pat. No. 7,501,389) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from 0.005 to 25 ppm, from 0.05 to 10 ppm, or from 0.1 to 5 ppm, of the MRL in the wash liquor.

Suitable transition-metals in the instant transition-metal bleach catalyst include e.g. manganese, iron and chromium. Suitable MRLs include 5,12-diethyl-1,5,8,12-tetraazabicyclo[6.6.2]hexadecane. Suitable transition metal MRLs are readily prepared by known procedures, such as taught e.g. in U.S. Pat. No. 6,225,464 and WO00/32601.

(7) Photobleaches—suitable photobleaches include e.g. sulfonated zinc phthalocyanine sulfonated aluminium phthalocyanines, xanthene dyes and mixtures thereof. Preferred bleach components for use in the present compositions of the invention comprise a hydrogen peroxide source, bleach activator and/or organic peroxyacid, optionally generated in situ by the reaction of a hydrogen peroxide source and bleach activator, in combination with a bleach catalyst. Preferred bleach components comprise bleach catalysts, preferably organic bleach catalysts, as described above.

Particularly preferred bleach components are the bleach catalysts in particular the organic bleach catalysts.

Exemplary bleaching systems are also described, e.g. in WO2007/087258, WO2007/087244, WO2007/087259 and WO2007/087242.

Fabric Hueing Agents—The composition may comprise a fabric hueing agent. Suitable fabric hueing agents include dyes, dye-clay conjugates, and pigments. Suitable dyes include small molecule dyes and polymeric dyes. Suitable small molecule dyes include small molecule dyes selected from the group consisting of dyes falling into the Color Index (C.I.) classifications of Direct Blue, Direct Red, Direct Violet, Acid Blue, Acid Red, Acid Violet, Basic Blue, Basic Violet and Basic Red, or mixtures thereof.

In another aspect, suitable small molecule dyes include small molecule dyes selected from the group consisting of Color Index (Society of Dyers and Colorists, Bradford, UK) numbers Direct Violet 9, Direct Violet 35, Direct Violet 48, Direct Violet 51, Direct Violet 66, Direct Violet 99, Direct Blue 1, Direct Blue 71, Direct Blue 80, Direct Blue 279, Acid Red 17, Acid Red 73, Acid Red 88, Acid Red 150, Acid Violet 15, Acid Violet 17, Acid Violet 24, Acid Violet 43, Acid Red 52, Acid Violet 49, Acid Violet 50, Acid Blue 15, Acid Blue 17, Acid Blue 25, Acid Blue 29, Acid Blue 40, Acid Blue 45, Acid Blue 75, Acid Blue 80, Acid Blue 83, Acid Blue 90 and Acid Blue 113, Acid Black 1, Basic Violet 1, Basic Violet 3, Basic Violet 4, Basic Violet 10, Basic Violet 35, Basic Blue 3, Basic Blue 16, Basic Blue 22, Basic Blue 47, Basic Blue 66, Basic Blue 75, Basic Blue 159 and mixtures thereof. In another aspect, suitable small molecule dyes include small molecule dyes selected from the group consisting of Color Index (Society of Dyers and Colorists, Bradford, UK) numbers Acid Violet 17, Acid Violet 43, Acid Red 52, Acid Red 73, Acid Red 88, Acid Red 150, Acid Blue 25, Acid Blue 29, Acid Blue 45, Acid Blue 113, Acid Black 1, Direct Blue 1, Direct Blue 71, Direct Violet 51 and mixtures thereof. In another aspect, suitable small molecule dyes include small molecule dyes selected from the group consisting of Color Index (Society of Dyers and Colorists, Bradford, UK) numbers Acid Violet 17, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing conjugated chromogens (dye-polymer conjugates) and polymers with chromogens co-polymerized into the backbone of the polymer and mixtures thereof.

In another aspect, suitable polymeric dyes include polymeric dyes selected from the group consisting of fabric-substantive colorants sold under the name of Liquitint® (Milliken), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colorants, alkoxylated thiophene polymeric colorants, and mixtures thereof.

Preferred hueing dyes include the whitening agents found in WO08/87497. These whitening agents may be characterized by the following structure (I):

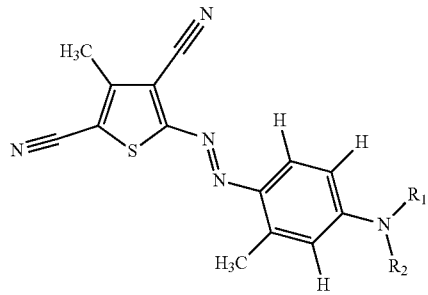

(I)

wherein R₁ and R₂ can independently be selected from:
a) [(CH₂CR'HO)ₓ(CH₂CR"HO)ᵧH]
wherein R' is selected from the group consisting of H, CH₃, CH₂O(CH₂CH₂O)$_z$H, and mixtures thereof; wherein R" is selected from the group consisting of H, CH₂O(CH₂CH₂O)$_z$H, and mixtures thereof; wherein x+y≤5; wherein y≥1; and wherein z=0 to 5;
b) R₁=alkyl, aryl or aryl alkyl and R₂=[(CH₂CR'HO)ₓ(CH₂CR"HO)ᵧH]
wherein R' is selected from the group consisting of H, CH₃, CH₂O(CH₂CH₂O)$_z$H, and mixtures thereof; wherein R" is selected from the group consisting of H, CH₂O(CH₂CH₂O)$_z$H, and mixtures thereof; wherein x+y≤10; wherein y≥1; and wherein z=0 to 5;
c) R₁=[CH₂CH₂(OR₃)CH₂OR₄] and R₂=[CH₂CH₂(OR₃)CH₂OR₄]
wherein R₃ is selected from the group consisting of H, (CH₂CH₂O)$_z$H, and mixtures thereof; and wherein z=0 to 10;
wherein R₄ is selected from the group consisting of (C₁-C₁₆)alkyl, aryl groups, and mixtures thereof; and
d) wherein R1 and R2 can independently be selected from the amino addition product of styrene oxide, glycidyl methyl ether, isobutyl glycidyl ether, isopropylglycidyl ether, t-butyl glycidyl ether, 2-ethylhexylgycidyl ether, and glycidylhexadecyl ether, followed by the addition of from 1 to 10 alkylene oxide units.

A preferred whitening agent of the present invention may be characterized by the following structure (II):

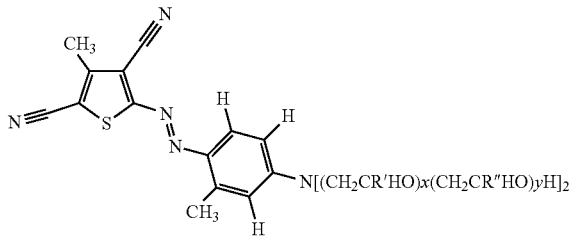

(II)

wherein R' is selected from the group consisting of H, CH₃, CH₂O(CH₂CH₂O)$_z$H, and mixtures thereof; wherein R" is selected from the group consisting of H, CH₂O(CH₂CH₂O)$_z$H, and mixtures thereof; wherein x+y≤5; wherein y≥1; and wherein z=0 to 5.

A further preferred whitening agent of the present invention may be characterized by the following structure (III):

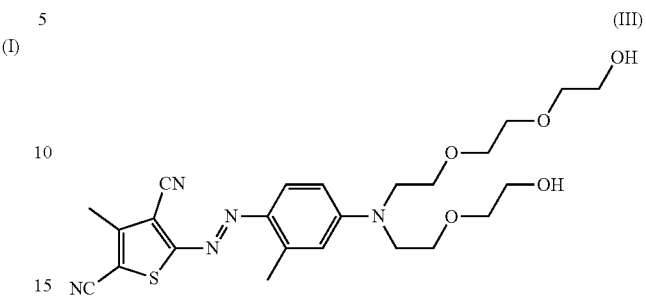

(III)

typically comprising a mixture having a total of 5 EO groups. Suitable preferred molecules are those in Structure I having the following pendant groups in "part a" above.

TABLE A

|   | R1 | | | | R2 | | | |
|---|---|---|---|---|---|---|---|---|
|   | R' | R" | x | y | R' | R" | x | y |
| a | H | H | 3 | 1 | H | H | 0 | 1 |
| b | H | H | 2 | 1 | H | H | 1 | 1 |
| c = b | H | H | 1 | 1 | H | H | 2 | 1 |
| d = a | H | H | 0 | 1 | H | H | 3 | 1 |

Further whitening agents of use include those described in US2008/34511 (Unilever). A preferred agent is "Violet 13".

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by C1-C3-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof.

In another aspect, suitable pigments include pigments selected from the group consisting of Ultramarine Blue (C.I. Pigment Blue 29), Ultramarine Violet (C.I. Pigment Violet 15) and mixtures thereof.

The aforementioned fabric hueing agents can be used in combination (any mixture of fabric hueing agents can be used). Suitable hueing agents are described in more detail in U.S. Pat. No. 7,208,459. Preferred levels of dye in compositions of the invention are 0.00001 to 0.5 wt %, or 0.0001 to 0.25 wt %. The concentration of dyes preferred in water for the treatment and/or cleaning step is from 1 ppb to 5 ppm, 10 ppb to 5 ppm or 20 ppb to 5 ppm. In preferred compositions, the concentration of surfactant will be from 0.2 to 3 g/l.

Encapsulates—The composition may comprise an encapsulate. In one aspect, an encapsulate comprising a core, a shell having an inner and outer surface, said shell encapsulating said core.

In one aspect of said encapsulate, said core may comprise a material selected from the group consisting of perfumes; brighteners; dyes; insect repellants; silicones; waxes; flavors; vitamins; fabric softening agents; skin care agents in one aspect, paraffins; enzymes; anti-bacterial agents; bleaches; sensates; and mixtures thereof; and said shell may comprise a material selected from the group consisting of polyethylenes; polyamides; polyvinylalcohols, optionally containing other co-monomers; polystyrenes; polyisoprenes; polycarbonates; polyesters; polyacrylates; aminoplasts, in one aspect said aminoplast may comprise a polyureas, polyurethane, and/or polyureaurethane, in one aspect said polyurea may comprise polyoxymethyleneurea and/or melamine formaldehyde; polyolefins; polysaccharides, in one aspect said polysaccharide may comprise alginate and/or chitosan; gelatin; shellac; epoxy resins; vinyl polymers; water insoluble inorganics; silicone; and mixtures thereof.

In one aspect of said encapsulate, said core may comprise perfume.

In one aspect of said encapsulate, said shell may comprise melamine formaldehyde and/or cross linked melamine formaldehyde.

In a one aspect, suitable encapsulates may comprise a core material and a shell, said shell at least partially surrounding said core material, is disclosed. 85% or 90% of said encapsulates may have a fracture strength of from 0.2 to 10 MPa, from 0.4 to 5 MPa, from 0.6 to 3.5 MPa, or from 0.7 to 3 MPa; and a benefit agent leakage of from 0 to 30%, from 0 to 20%, or from 0 to 5%.

In one aspect, 85% or 90% of said encapsulates may have a particle size from 1 to 80 microns, from 5 to 60 microns, from 10 to 50 microns, or from 15 to 40 microns.

In one aspect, 85% or 90% of said encapsulates may have a particle wall thickness from 30 to 250 nm, from 80 to 180 nm, or from 100 to 160 nm.

In one aspect, said encapsulates' core material may comprise a material selected from the group consisting of a perfume raw material and/or optionally a material selected from the group consisting of vegetable oil, including neat and/or blended vegetable oils including castor oil, coconut oil, cottonseed oil, grape oil, rapeseed, soybean oil, corn oil, palm oil, linseed oil, safflower oil, olive oil, peanut oil, coconut oil, palm kernel oil, castor oil, lemon oil and mixtures thereof; esters of vegetable oils, esters, including dibutyl adipate, dibutyl phthalate, butyl benzyl adipate, benzyl octyl adipate, tricresyl phosphate, trioctyl phosphate and mixtures thereof; straight or branched chain hydrocarbons, including those straight or branched chain hydrocarbons having a boiling point of greater than about 80° C.; partially hydrogenated terphenyls, dialkyl phthalates, alkyl biphenyls, including monoisopropylbiphenyl, alkylated naphthalene, including dipropylnaphthalene, petroleum spirits, including kerosene, mineral oil and mixtures thereof; aromatic solvents, including benzene, toluene and mixtures thereof; silicone oils; and mixtures thereof.

In one aspect, said encapsulates' wall material may comprise a suitable resin including the reaction product of an aldehyde and an amine, suitable aldehydes include, formaldehyde. Suitable amines include melamine, urea, benzoguanamine, glycoluril, and mixtures thereof. Suitable melamines include methylol melamine, methylated methylol melamine, imino melamine and mixtures thereof. Suitable ureas include dimethylol urea, methylated dimethylol urea, urea-resorcinol, and mixtures thereof.

In one aspect, suitable formaldehyde scavengers may be employed with the encapsulates e.g. in a capsule slurry and/or added to a composition before, during or after the encapsulates are added to such composition. Suitable capsules may be made by the following teaching of US2008/0305982; and/or US2009/0247449.

In a preferred aspect the composition can also comprise a deposition aid, preferably consisting of the group comprising cationic or nonionic polymers. Suitable polymers include cationic starches, cationic hydroxyethylcellulose, polyvinylformaldehyde, locust bean gum, mannans, xyloglucans, tamarind gum, polyethyleneterephthalate and polymers containing dimethylaminoethyl methacrylate, optionally with one or monomers selected from the group comprising acrylic acid and acrylamide.

Perfumes—In one aspect the composition comprises a perfume that comprises one or more perfume raw materials selected from the group consisting of 1,1'-oxybis-2-propanol; 1,4-cyclohexanedicarboxylic acid, diethyl ester; (ethoxymethoxy)cyclododecane; 1,3-nonanediol, monoacetate; (3-methylbutoxy)acetic acid, 2-propenyl ester; beta-methyl cyclododecaneethanol; 2-methyl-3-[(1,7,7-trimethylbicyclo[2.2.1]hept-2-yl)oxy]-1-propanol; oxacyclohexadecan-2-one; alpha-methyl-benzenemethanol acetate; trans-3-ethoxy-1,1,5-trimethylcyclohexane; 4-(1,1-dimethylethyl)cyclohexanol acetate; dodecahydro-3a,6,6,9a-tetramethylnaphtho[2,1-b]furan; beta-methyl benzenepropanal; beta-methyl-3-(1-methylethyl) benzenepropanal; 4-phenyl-2-butanone; 2-methylbutanoic acid, ethyl ester; benzaldehyde; 2-methylbutanoic acid, 1-methylethyl ester; dihydro-5-pentyl-2(3H)furanone; (2E)-1-(2,6,6-trimethyl-2-cyclohexen-1-yl)-2-buten-1-one; dodecanal; undecanal; 2-ethyl-alpha, alpha-dimethylbenzenepropanal; decanal; alpha, alpha-dimethylbenzeneethanol acetate; 2-(phenylmethylene)octanal; 2-[[3-[4-(1,1-dimethylethyl)phenyl]-2-methylpropylidene]amino]benzoic acid, methyl ester; 1-(2,6,6-trimethyl-3-cyclohexen-1-yl)-2-buten-1-one; 2-pentylcyclopentanone; 3-oxo-2-pentyl cyclopentaneacetic acid, methyl ester; 4-hydroxy-3-methoxybenzaldehyde; 3-ethoxy-4-hydroxybenzaldehyde; 2-heptylcyclopentanone; 1-(4-methylphenyl)ethanone;

(3E)-4-(2,6,6-trimethyl-1-cyclohexen-1-yl)-3-buten-2-one; (3E)-4-(2,6,6-trimethyl-2-cyclohexen-1-yl)-3-buten-2-one; benzeneethanol; 2H-1-benzopyran-2-one; 4-methoxybenzaldehyde; 10-undecenal; propanoic acid, phenylmethyl ester; beta-methylbenzenepentanol; 1,1-diethoxy-3,7-dimethyl-2,6-octadiene; alpha, alpha-dimethylbenzeneethanol; (2E)-1-(2,6,6-trimethyl-1-cyclohexen-1-yl)-2-buten-1-one; acetic acid, phenylmethyl ester; cyclohexanepropanoic acid, 2-propenyl ester; hexanoic acid, 2-propenyl ester; 1,2-dimethoxy-4-(2-propenyl)benzene; 1,5-dimethyl-bicyclo[3.2.1]octan-8-one oxime; 4-(4-hydroxy-4-methylpentyl)-3-cyclohexene-1-carboxaldehyde; 3-buten-2-ol; 2-[[[2,4(or 3,5)-dimethyl-3-cyclohexen-1-yl]methylene]amino]benzoic acid, methyl ester; 8-cyclohexadecen-1-one; methyl ionone; 2,6-dimethyl-7-octen-2-ol; 2-methoxy-4-(2-propenyl)phenol; (2E)-3,7-dimethyl-2,6-Octadien-1-ol; 2-hydroxy-Benzoic acid, (3Z)-3-hexenyl ester; 2-tridecenenitrile; 4-(2,2-dimethyl-6-methylenecyclohexyl)-3-methyl-3-buten-2-one; tetrahydro-4-methyl-2-(2-methyl-1-propenyl)-2H-pyran; Acetic acid, (2-methylbutoxy)-, 2-propenyl ester; Benzoic acid, 2-hydroxy-, 3-methylbutyl ester; 2-Buten-1-one, 1-(2, 6,6-trimethyl-1-cyclohexen-1-yl)-, (Z)-; Cyclopentanecarboxylic acid, 2-hexyl-3-oxo-, methyl ester; Benzenepropanal, 4-ethyl-.alpha., .alpha.-dimethyl-; 3-Cyclohexene-1-carboxaldehyde, 3-(4-hydroxy-4-methylpentyl)-; Ethanone, 1-(2,3,4,7,8,8a-hexahydro-3,6,8,8-tetramethyl-1H-3a,7-methanoazulen-5-yl)-, [3R-(3.alpha.,3a.beta.,7.beta.,8a.alpha.)]-; Undecanal, 2-methyl-2H-Pyran-2-one, 6-butyltetrahydro-; Benzenepropanal, 4-(1,1-dimethylethyl)-.alpha.-methyl-; 2(3H)-Furanone, 5-heptyldihydro-; Benzoic acid, 2-[(7-hydroxy-3,7-dimethyloctylidene)amino]-, methyl; Benzoic acid, 2-hydroxy-, phenylmethyl ester; Naphthalene, 2-methoxy-; 2-Cyclopenten-1-one, 2-hexyl-; 2(3H)-Furanone, 5-hexyldihydro-; Oxiranecarboxylic acid, 3-methyl-3-phenyl-, ethyl ester; 2-Oxabicyclo[2.2.2]octane, 1,3,3-trimethyl-; Benzenepentanol, .gamma.-methyl-; 3-Octanol, 3,7-dimethyl-; 3,7-dimethyl-2,6-octadienenitrile; 3,7-dimethyl-6-octen-1-ol; Terpineol acetate; 2-methyl-6-methylene-7-Octen-2-ol, dihydro derivative; 3a,4,5,6,7,7a-hexahydro-4,7-Methano-1H-inden-6-ol propanoate; 3-methyl-2-buten-1-ol acetate; (Z)-3-Hexen-1-ol acetate; 2-ethyl-4-(2, 2,3-trimethyl-3-cyclopenten-1-yl)-2-buten-1-ol; 4-(octahydro-4,7-methano-5H-inden-5-ylidene)-butanal; 3-2,4-dimethyl-cyclohexene-1-carboxaldehyde; 1-(1,2,3,4, 5,6,7,8-octahydro-2,3,8,8-tetramethyl-2-naphthalenyl)-ethanone; 2-hydroxy-benzoic acid, methyl ester; 2-hydroxy-benzoic acid, hexyl ester; 2-phenoxy-ethanol; 2-hydroxy-benzoic acid, pentyl ester; 2,3-heptanedione; 2-hexen-1-ol; 6-Octen-2-ol, 2,6-dimethyl-; damascone (alpha, beta, gamma or delta or mixtures thereof), 4,7-Methano-1H-inden-6-ol, 3a,4,5,6,7,7a-hexahydro-, acetate; 9-Undecenal; 8-Undecenal; Isocyclocitral; Ethanone, 1-(1,2,3,5,6,7,8,8a-octahydro-2,3,8,8-tetramethyl-2-naphthalenyl)-; 3-Cyclohexene-1-carboxaldehyde, 3,5-dimethyl-; 3-Cyclohexene-1-carboxaldehyde, 2,4-dimethyl-; 1,6-Octadien-3-ol, 3,7-dimethyl-; 1,6-Octadien-3-ol, 3,7-dimethyl-, acetate; Lilial (p-t-Bucinal), and Cyclopentanone, 2-[2-(4-methyl-3-cyclohexen-1-yl)propyl]- and 1-methyl-4-(1-methylethenyl)cyclohexene and mixtures thereof.

In one aspect the composition may comprise an encapsulated perfume particle comprising either a water-soluble hydroxylic compound or melamine-formaldehyde or modified polyvinyl alcohol. In one aspect the encapsulate comprises (a) an at least partially water-soluble solid matrix comprising one or more water-soluble hydroxylic compounds, preferably starch; and (b) a perfume oil encapsulated by the solid matrix.

In a further aspect the perfume may be pre-complexed with a polyamine, preferably a polyethylenimine so as to form a Schiff base.

Polymers—The composition may comprise one or more polymers. Examples are carboxymethylcellulose, poly(vinyl-pyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers.

The composition may comprise one or more amphiphilic cleaning polymers such as the compound having the following general structure: bis$((C_2H_5O)(C_2H_4O)n)(CH_3)$—$N^+$—$C_xH_{2x}$—$N^+$—$(CH_3)$-bis$((C_2H_5O)(C_2H_4O)n)$, wherein n=from 20 to 30, and x=from 3 to 8, or sulphated or sulphonated variants thereof.

The composition may comprise amphiphilic alkoxylated grease cleaning polymers which have balanced hydrophilic and hydrophobic properties such that they remove grease particles from fabrics and surfaces. Specific embodiments of the amphiphilic alkoxylated grease cleaning polymers of the present invention comprise a core structure and a plurality of alkoxylate groups attached to that core structure. These may comprise alkoxylated polyalkylenimines, preferably having an inner polyethylene oxide block and an outer polypropylene oxide block.

Alkoxylated polycarboxylates such as those prepared from polyacrylates are useful herein to provide additional grease removal performance. Such materials are described in WO91/08281 and PCT90/01815. Chemically, these materials comprise polyacrylates having one ethoxy side-chain per every 7-8 acrylate units. The side-chains are of the formula —$(CH_2CH_2O)_m(CH_2)_nCH_3$ wherein m is 2-3 and n is 6-12. The side-chains are ester-linked to the polyacrylate "backbone" to provide a "comb" polymer type structure. The molecular weight can vary, but is typically in the range of 2000 to 50,000. Such alkoxylated polycarboxylates can comprise from 0.05 wt % to 10 wt % of the compositions herein.

The isoprenoid-derived surfactants of the present invention, and their mixtures with other cosurfactants and other adjunct ingredients, are particularly suited to be used with an amphilic graft co-polymer, preferably the amphilic graft co-polymer comprises (i) polyethyelene glycol backbone; and (ii) and at least one pendant moiety selected from polyvinyl acetate, polyvinyl alcohol and mixtures thereof. A preferred amphilic graft co-polymer is Sokalan HP22, supplied from BASF. Suitable polymers include random graft copolymers, preferably a polyvinyl acetate grafted polyethylene oxide copolymer having a polyethylene oxide backbone and multiple polyvinyl acetate side chains. The molecular weight of the polyethylene oxide backbone is preferably 6000 and the weight ratio of the polyethylene oxide to polyvinyl acetate is 40 to 60 and no more than 1 grafting point per 50 ethylene oxide units.

Carboxylate polymer—The composition of the present invention may also include one or more carboxylate polymers such as a maleate/acrylate random copolymer or polyacrylate homopolymer. In one aspect, the carboxylate polymer is a polyacrylate homopolymer having a molecular weight of from 4,000 to 9,000 Da, or from 6,000 to 9,000 Da.

Soil release polymer—The composition of the present invention may also include one or more soil release polymers having a structure as defined by one of the following structures (I), (II) or (III):

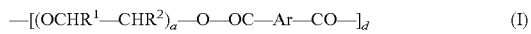

(I)

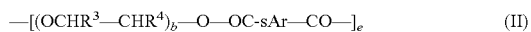

(II)

(III)

wherein:
a, b and c are from 1 to 200;
d, e and f are from 1 to 50;
Ar is a 1,4-substituted phenylene;
sAr is 1,3-substituted phenylene substituted in position 5 with $SO_3Me$;
Me is Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or mixtures thereof;
$R^1$, $R^2$, $R^3$, $R^4$, $R^5$ and $R^6$ are independently selected from H or $C_1$-$C_{18}$ n- or iso-alkyl; and
$R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group.

Suitable soil release polymers are polyester soil release polymers such as Repel-o-tex polymers, including Repel-o-tex, SF-2 and SRP6 supplied by Rhodia. Other suitable soil release polymers include Texcare polymers, including Texcare SRA100, SRA300, SRN100, SRN170, SRN240, SRN300 and SRN325 supplied by Clariant. Other suitable soil release polymers are Marloquest polymers, such as Marloquest SL supplied by Sasol.

Cellulosic polymer—The composition of the present invention may also include one or more cellulosic polymers including those selected from alkyl cellulose, alkyl alkoxyalkyl cellulose, carboxyalkyl cellulose, alkyl carboxyalkyl cellulose. In one aspect, the cellulosic polymers are selected from the group comprising carboxymethyl cellulose, methyl cellulose, methyl hydroxyethyl cellulose, methyl carboxymethyl cellulose, and mixures thereof. In one aspect, the carboxymethyl cellulose has a degree of carboxymethyl substitution from 0.5 to 0.9 and a molecular weight from 100,000 to 300,000 Da.

Enzymes—The composition may comprise one or more additional enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, xanthanase, ligninases, pullulanases, tannases, pentosanases, malanases, β-glucanases, arabinosidases, hyaluronidase, chondroitinase, laccase, chlorophyllases and amylases, or mixtures thereof. A typical combination is an enzyme cocktail that may comprise e.g. a protease and lipase in conjunction with amylase. When present in a composition, the aforementioned additional enzymes may be present at levels from 0.00001 to 2 wt %, from 0.0001 to 1 wt % or from 0.001 to 0.5 wt % enzyme protein by weight of the composition.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases—Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g., the fungal cellulases produced from Humicola insolens, Myceliophthora thermophila and Fusarium oxysporum disclosed in U.S. Pat. Nos. 4,435,307, 5,648,263, 5,691,178, 5,776,757 and WO89/09259.

Especially suitable cellulases are the alkaline or neutral cellulases having colour care benefits. Examples of such cellulases are cellulases described in EP0495257, EP0531372, WO96/11262, WO96/29397, and WO98/08940. Other examples are cellulase variants such as those described in WO94/07998, EP0531315, U.S. Pat. Nos. 5,457,046, 5,686,593, 5,763,254, WO95/24471, WO98/12307 and WO99/001544.

Other cellulases are endo-beta-1,4-glucanase enzyme having a sequence of at least 97% identity to the amino acid sequence of position 1 to position 773 of SEQ ID NO:2 of WO02/099091 or a family 44 xyloglucanase, which a xyloglucanase enzyme having a sequence of at least 60% identity to positions 40-559 of SEQ ID NO: 2 of WO01/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Proteases—Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from Bacillus such as Bacillus lentus, B. alkalophilus, B. subtilis, B. amyloliquefaciens, Bacillus pumilus and Bacillus gibsonii described in; U.S. Pat. No. 7,262,042 and WO09/021867, and subtilisin lentus, subtilisin Novo, subtilisin Carlsberg, Bacillus licheniformis, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the Fusarium protease described in WO89/06270, WO94/25583 and WO05/040372, and the chymotrypsin proteases derived from Cellumonas described in WO05/052161 and WO05/052146.

A further preferred protease is the alkaline protease from Bacillus lentus DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V4I, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect Ox®, Puramax®, Properase®, Effectenz™, FN2®, FN3®, FN4®, Excellase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases—Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases—Suitable amylases which can be used together with the enzyme/variant/blend of enzymes of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB1296839.

Suitable amylases include amylases having SEQ ID NO: 2 in WO95/10603 or variants having 90% sequence identity to SEQ ID NO: 3 thereof. Preferred variants are described in WO94/02597, WO94/18314, WO97/43424 and SEQ ID NO: 4 of WO99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO06/066594 and residues 36-483 of the *B. licheniformis* alpha-amylase shown in SEQ ID NO: 4 of WO06/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO06/066594 and residues 36-483 of SEQ ID NO: 4 are those having the substitutions:
M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO08/153815, SEQ ID NO: 10 in WO 01/66712 or variants thereof having 90% sequence identity to SEQ ID NO: 2 of WO08/153815 or 90% sequence identity to SEQ ID NO: 10 in WO01/66712. Preferred variants of SEQ ID NO: 10 in WO01/66712 are those having a substitution, a deletion or an insertion in one of more of the following positions: 176, 177, 178, 179, 190, 201, 207, 211 and 264.

Further suitable amylases are amylases having SEQ ID NO: 2 of WO09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:
N128C+K178L+T182G+Y305R+G475K;
N 128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

Peroxidases/Oxidases—Suitable peroxidases according to the invention is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP179486), and variants thereof as those described in WO93/24618, WO95/10602, and WO98/15257.

A peroxidase also includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as *Caldariomyces*, e.g., *C. fumago*, *Alternaria*, *Curvularia*, e.g., *C. verruculosa* and *C. inaequalis*, *Drechslera*, *Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In an preferred embodiment, the haloperoxidase is derivable from *Curvularia* sp., in particular *Curvularia verruculosa* or *Curvularia inaequalis*, such as *C. inaequalis* CBS 102.42 as described in WO95/27046; or *C. verruculosa* CBS 147.63 or *C. verruculosa* CBS 444.70 as described in WO97/04102; or from *Drechslera hartlebii* as described in WO01/79459, *Dendryphiella salina* as described in WO01/79458, *Phaeotrichoconis crotalarie* as described in WO01/79461, or *Geniculosporium* sp. as described in WO01/79460.

An oxidase according to the invention include, in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be derived from plants, bacteria or fungi (including filamentous fungi and yeasts).

Suitable examples from fungi include a laccase derivable from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizoctonia*, e.g., *R. solani*, *Coprinopsis*, e.g., *C. cinerea*, *C. comatus*, *C. friesii*, and *C. plicatilis*, *Psathyrella*, e.g., *P. condelleana*, *Panaeolus*, e.g., *P. papilionaceus*, *Myceliophthora*, e.g., *M. thermophila*, *Schytalidium*, e.g., *S. thermophilum*, *Polyporus*, e.g., *P. pinsitus*, *Phiebia*, e.g., *P. radiata* (WO92/01046), or *Coriolus*, e.g., *C. hirsutus* (JP2238885).

Suitable examples from bacteria include a laccase derivable from a strain of *Bacillus*. A laccase derived from *Coprinopsis* or *Myceliophthora* is preferred; in particular a laccase derived from *Coprinopsis cinerea*, as disclosed in WO97/08325; or from *Myceliophthora thermophila*, as disclosed in WO95/33836.

Other preferred enzymes include pectate lyases sold under the tradenames Pectawash®, Pectaway®, Xpect® and mannanases sold under the tradenames Mannaway® (Novozymes), and Purabrite® (Danisco/Dupont).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP238216.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a composition, the dye transfer inhibiting agents may be present at levels from 0.0001 to 10 wt %, from 0.01 to 5 wt % or from 0.1 to 3 wt %.

Brighteners—The compositions of the present invention can also contain additional components that may tint articles being cleaned, such as fluorescent brighteners.

The composition may comprise C.I. fluorescent brightener 260 in alpha-crystalline form having the following structure:

dominantly in alpha-crystalline form, which means that typically at least 50 wt %, at least 75 wt %, at least 90 wt %, at least 99 wt %, or even substantially all, of the C.I. fluorescent brightener 260 is in alpha-crystalline form.

The brightener is typically in micronized particulate form, having a weight average primary particle size of from 3 to 30 micrometers, from 3 micrometers to 20 micrometers, or from 3 to 10 micrometers.

The composition may comprise C.I. fluorescent brightener 260 in beta-crystalline form, and the weight ratio of: (i) C.I. fluorescent brightener 260 in alpha-crystalline form, to (ii) C.I. fluorescent brightener 260 in beta-crystalline form may be at least 0.1, or at least 0.6. BE680847 relates to a process for making C.I. fluorescent brightener 260 in alpha-crystalline form.

Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982). Specific nonlimiting examples of optical brighteners which are useful in the present compositions are those identified in U.S. Pat. Nos. 4,790,856 and 3,646,015.

A further suitable brightener has the structure below:

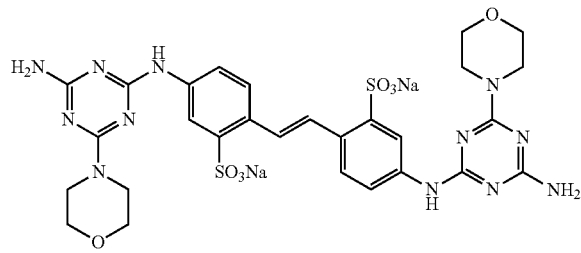

Suitable fluorescent brightener levels include lower levels of from 0.01 wt %, from 0.05 wt %, from 0.1 wt % or from 0.2 wt % to upper levels of 0.5 wt % or 0.75 wt %.

In one aspect the brightener may be loaded onto a clay to form a particle. Silicate salts—The compositions of the present invention can also contain silicate salts, such as sodium or potassium silicate. The composition may com-

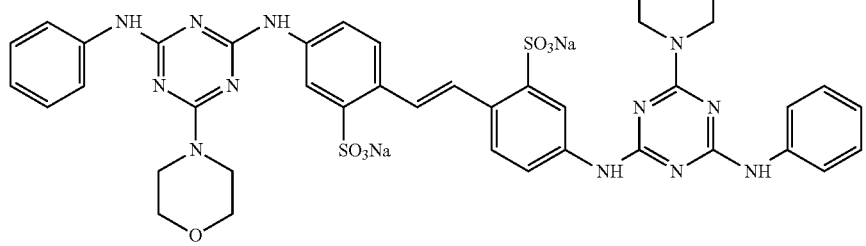

In one aspect, the brightener is a cold water soluble brightener, such as the C.I. fluorescent brightener 260 in alpha-crystalline form. In one aspect the brightener is preprise of from 0 wt % to less than 10 wt % silicate salt, to 9 wt %, or to 8 wt %, or to 7 wt %, or to 6 wt %, or to 5 wt %, or to 4 wt %, or to 3 wt %, or even to 2 wt %, and from above 0 wt %, or from 0.5 wt %, or from 1 wt % silicate salt. A suitable silicate salt is sodium silicate.

Dispersants—The compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

Enzyme Stabilizers—Enzymes for use in compositions can be stabilized by various techniques. The enzymes employed herein can be stabilized by the presence of water-soluble sources of calcium and/or magnesium ions. Examples of conventional stabilizing agents are, e.g. a polyol such as propylene glycol or glycerol, a sugar or sugar alcohol, lactic acid, boric acid, or a boric acid derivative, e.g. an aromatic borate ester, or a phenyl boronic acid derivative such as 4-formylphenyl boronic acid, and the composition may be formulated as described in, for example, WO92/19709 and WO92/19708 In case of aqueous compositions comprising protease, a reversible protease inhibitor, such as a boron compound including borate, 4-formyl phenylboronic acid, phenylboronic acid and derivatives thereof, or compounds such as calcium formate, sodium formate and 1,2-propane diol can be added to further improve stability.

Solvents—Suitable solvents include water and other solvents such as lipophilic fluids. Examples of suitable lipophilic fluids include siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures thereof.

Structurant/Thickeners—Structured liquids can either be internally structured, whereby the structure is formed by primary ingredients (e.g. surfactant material) and/or externally structured by providing a three dimensional matrix structure using secondary ingredients (e.g. polymers, clay and/or silicate material). The composition may comprise a structurant, from 0.01 to 5 wt %, or from 0.1 to 2.0 wt %. The structurant is typically selected from the group consisting of diglycerides and triglycerides, ethylene glycol distearate, microcrystalline cellulose, cellulose-based materials, microfiber cellulose, hydrophobically modified alkali-swellable emulsions such as Polygel W30 (3VSigma), biopolymers, xanthan gum, gellan gum, and mixtures thereof. A suitable structurant includes hydrogenated castor oil, and non-ethoxylated derivatives thereof. A suitable structurant is disclosed in U.S. Pat. No. 6,855,680. Such structurants have a thread-like structuring system having a range of aspect ratios. Other suitable structurants and the processes for making them are described in WO10/034736.

Conditioning Agents—The composition of the present invention may include a high melting point fatty compound. The high melting point fatty compound useful herein has a melting point of 25° C. or higher, and is selected from the group consisting of fatty alcohols, fatty acids, fatty alcohol derivatives, fatty acid derivatives, and mixtures thereof. Such compounds of low melting point are not intended to be included in this section. Non-limiting examples of the high melting point compounds are found in International Cosmetic Ingredient Dictionary, Fifth Edition, 1993, and CTFA Cosmetic Ingredient Handbook, Second Edition, 1992.

The high melting point fatty compound is included in the composition at a level of from 0.1 to 40 wt %, from 1 to 30 wt %, from 1.5 to 16 wt %, from 1.5 to 8 wt % in view of providing improved conditioning benefits such as slippery feel during the application to wet hair, softness and moisturized feel on dry hair.

The compositions of the present invention may contain a cationic polymer. Concentrations of the cationic polymer in the composition typically range from 0.05 to 3 wt %, from 0.075 to 2.0 wt %, or from 0.1 to 1.0 wt %. Suitable cationic polymers will have cationic charge densities of at least 0.5 meq/gm, at least 0.9 meq/gm, at least 1.2 meq/gm, at least 1.5 meq/gm, or less than 7 meq/gm, and less than 5 meq/gm, at the pH of intended use of the composition, which pH will generally range from pH3 to pH9, or between pH4 and pH8. Herein, "cationic charge density" of a polymer refers to the ratio of the number of positive charges on the polymer to the molecular weight of the polymer. The average molecular weight of such suitable cationic polymers will generally be between 10,000 and 10 million, between 50,000 and 5 million, or between 100,000 and 3 million.

Suitable cationic polymers for use in the compositions of the present invention contain cationic nitrogen-containing moieties such as quaternary ammonium or cationic protonated amino moieties. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair composition performance, stability or aesthetics. Nonlimiting examples of such counterions include halides (e.g., chloride, fluoride, bromide, iodide), sulfate and methylsulfate.

Nonlimiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Other suitable cationic polymers for use in the composition include polysaccharide polymers, cationic guar gum derivatives, quaternary nitrogen-containing cellulose ethers, synthetic polymers, copolymers of etherified cellulose, guar and starch. When used, the cationic polymers herein are either soluble in the composition or are soluble in a complex coacervate phase in the composition formed by the cationic polymer and the anionic, amphoteric and/or zwitterionic surfactant component described hereinbefore. Complex coacervates of the cationic polymer can also be formed with other charged materials in the composition. Suitable cationic polymers are described in U.S. Pat. Nos. 3,962,418; 3,958,581; and US2007/0207109.

The composition of the present invention may include a nonionic polymer as a conditioning agent. Polyalkylene glycols having a molecular weight of more than 1000 are useful herein. Useful are those having the following general formula:

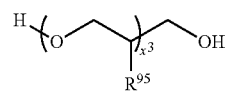

wherein $R^{95}$ is selected from the group consisting of H, methyl, and mixtures thereof. Conditioning agents, and in particular silicones, may be included in the composition. The conditioning agents useful in the compositions of the present invention typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair composition stability, aesthetics or performance.

The concentration of the conditioning agent in the composition should be sufficient to provide the desired conditioning benefits. Such concentration can vary with the conditioning agent, the conditioning performance desired, the average size of the conditioning agent particles, the type and concentration of other components, and other like factors.

The concentration of the silicone conditioning agent typically ranges from 0.01 to 10 wt %. Non-limiting examples of suitable silicone conditioning agents, and optional suspending agents for the silicone, are described in U.S. Reissue Pat. No. 34,584; U.S. Pat. Nos. 5,104,646; 5,106,609; 4,152,416; 2,826,551; 3,964,500; 4,364,837; 6,607,717; 6,482,969; 5,807,956; 5,981,681; 6,207,782; 7,465,439; 7,041,767; 7,217,777; US2007/0286837A1; US2005/0048549A1; US2007/0041929A1; GB849433; DE10036533, which are all incorporated herein by reference; Chemistry and Technology of Silicones, New York: Academic Press (1968); General Electric Silicone Rubber Product Data Sheets SE 30, SE 33, SE 54 and SE 76; Silicon Compounds, Petrarch Systems, Inc. (1984); and in Encyclopedia of Polymer Science and Engineering, vol. 15, 2d ed., pp 204-308, John Wiley & Sons, Inc. (1989).

The compositions of the present invention may also comprise from 0.05 to 3 wt % of a at least one organic conditioning oil as the conditioning agent, either alone or in combination with other conditioning agents, such as the silicones (described herein). Suitable conditioning oils include hydrocarbon oils, polyolefins, and fatty esters. Also suitable for use in the compositions herein are the conditioning agents described in U.S. Pat. Nos. 5,674,478, 5,750, 122 or in U.S. Pat. Nos. 4,529,586; 4,507,280; 4,663,158; 4,197,865; 4,217,914; 4,381,919; and 4,422,853.

Hygiene and malodour—The compositions of the present invention may also comprise one or more of zinc ricinoleate, thymol, quaternary ammonium salts such as Bardac®, polyethylenimines (such as Lupasol® from BASF) and zinc complexes thereof, silver and silver compounds, especially those designed to slowly release $Ag^+$ or nano-silver dispersions.

Probiotics—The compositions may comprise probiotics such as those described in WO09/043709.

Suds Boosters—If high sudsing is desired, suds boosters such as the $C_{10}$-$C_{16}$ alkanolamides or $C_{10}$-$C_{14}$ alkyl sulphates can be incorporated into the compositions, typically at 1 to 10 wt % levels. The $C_{10}$-$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, water-soluble magnesium and/or calcium salts such as $MgCl_2$, $MgSO_4$, $CaCl_2$, $CaSO_4$ and the like, can be added at levels of, typically, 0.1 to 2 wt %, to provide additional suds and to enhance grease removal performance.

Suds Suppressors—Compounds for reducing or suppressing the formation of suds can be incorporated into the compositions of the present invention. Suds suppression can be of particular importance in the so-called "high concentration cleaning process" as described in U.S. Pat. Nos. 4,489,455 and 4,489,574, and in front-loading-style washing machines. A wide variety of materials may be used as suds suppressors, and suds suppressors are well known to those skilled in the art. See e.g. Kirk Othmer Encyclopedia of Chemical Technology, Third Edition, Volume 7, p. 430-447 (John Wiley & Sons, Inc., 1979). Examples of suds supressors include monocarboxylic fatty acid and soluble salts therein, high molecular weight hydrocarbons such as paraffin, fatty acid esters (e.g., fatty acid triglycerides), fatty acid esters of monovalent alcohols, aliphatic $C_{18}$-$C_{40}$ ketones (e.g., stearone), N-alkylated amino triazines, waxy hydrocarbons preferably having a melting point below about 100° C., silicone suds suppressors, and secondary alcohols. Suds supressors are described in U.S. Pat. Nos. 2,954,347; 4,265, 779; 4,265,779; 3,455,839; 3,933,672; 4,652,392; 4,978, 471; 4,983,316; 5,288,431; 4,639,489; 4,749,740; 4,798, 679; 4,075,118; EP89307851.9; EP150872; and DOS 2,124, 526.

For any detergent compositions to be used in automatic laundry washing machines, suds should not form to the extent that they overflow the washing machine. Suds suppressors, when utilized, are preferably present in a "suds suppressing amount. By "suds suppressing amount" is meant that the formulator of the composition can select an amount of this suds controlling agent that will sufficiently control the suds to result in a low-sudsing laundry detergent for use in automatic laundry washing machines.

The compositions herein will generally comprise from 0 to 10 wt % of suds suppressor. When utilized as suds suppressors, monocarboxylic fatty acids, and salts therein, will be present typically in amounts up to 5 wt %. Preferably, from 0.5 to 3 wt % of fatty monocarboxylate suds suppressor is utilized. Silicone suds suppressors are typically utilized in amounts up to 2.0 wt %, although higher amounts may be used. Monostearyl phosphate suds suppressors are generally utilized in amounts ranging from 0.1 to 2 wt %. Hydrocarbon suds suppressors are typically utilized in amounts ranging from 0.01 to 5.0 wt %, although higher levels can be used. The alcohol suds suppressors are typically used at 0.2 to 3 wt %. The compositions herein may have a cleaning activity over a broad range of pH. In certain embodiments the compositions have cleaning activity from pH4 to pH11.5. In other embodiments, the compositions are active from pH6 to pH11, from pH7 to pH11, from pH8 to pH11, from pH9 to pH11, or from pH10 to pH11.5.

The compositions herein may have cleaning activity over a wide range of temperatures, e.g., from 10° C. or lower to 90° C. Preferably the temperature will be below 50° C. or 40° C. or even 30° C. In certain embodiments, the optimum temperature range for the compositions is from 10° C. to 20° C., from 15° C. to 25° C., from 15° C. to 30° C., from 20° C. to 30° C., from 25° C. to 35° C., from 30° C. to 40° C., from 35° C. to 45° C., or from 40° C. to 50° C.

Form of the Detergent Composition

The detergent compositions described herein are advantageously employed for example, in laundry applications for private house hold as well as in industrial and institutional cleaning. The compositions of the invention are in particular solid or liquid cleaning and/or treatment compositions. In one aspect the invention relates to a composition, wherein the form of the composition is selected from the group consisting of a regular, compact or concentrated liquid; a gel; a paste; a soap bar; a regular or a compacted powder; a granulated solid; a homogenous or a multilayer tablet with two or more layers (same or different phases); a pouch having one or more compartments; a single or a multi-compartment unit dose form; or any combination thereof.

The form of the composition may separate the components physically from each other in compartments such as e.g. water dissolvable pouches or in different layers of tablets. Thereby negative storage interaction between components can be avoided. Different dissolution profiles of each of the compartments can also give rise to delayed dissolution of selected components in the wash solution.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids (US2009/0011970 A1).

Lipase Particles

The lipase variants comprised in the water-soluble film of the invention may be present as lipase particles. The lipase particles may even contain one or more Additional Enzymes, as described below.

Lipase particles are any form of lipase variant in a solid particulate form. That can be as lipase crystals, lipase precipitate, spray or freeze-dried lipase or any form of granulated lipase, either as a powder or a suspension in liquid. Typically the particle size, measured as equivalent spherical diameter (volume based average particle size), of the lipase particles is below 2 mm, preferably below 1 mm, below 0.5 mm, below 0.25 mm, or below 0.1 mm; and above 0.05 µm, preferably above 0.1 µm, above 0.5 µm, above 1 µm, above 5 µm or above 10 µm.

In a preferred embodiment, the particle size of the lipase particles is from 0.5 µm to 100 µm.

The lipase particles contain at least 1% w/w lipase protein, preferably at least 5% w/w lipase protein, at least 10% w/w lipase protein, at least 20% w/w lipase protein, at least 30% w/w lipase protein, at least 40% w/w lipase protein, at least 50% w/w lipase protein, at least 60% w/w lipase protein, at least 70% w/w lipase protein, at least 80% w/w lipase protein, or at least 90% w/w lipase protein.

In a preferred embodiment, the lipase particles are lipase crystals, or the lipase protein is on a crystalline form.

Enzyme crystallization may be carried out in a number of ways, as known in the art (e.g., as described in WO91/09943 or WO94/22903).

The lipase may be formulated in the lipase particle as known in the art for solid enzyme formulations, such as formulations for reducing dust, improving stability and/or modifying relase rate of the enzyme. The lipase particle may also be formulated in a matrix or coated with agents suppressing dissolution of the enzyme particle in the PVOH/film solution used for preparing the water-soluble film.

The lipase molecules on the surface of the lipase particles may also be cross-linked, like CLECs (Cross-Linked Enzyme Crystals) or CLEA (Cross-Linked Enzyme Aggregate).

Water-Soluble Film

Water-soluble films, optional ingredients for use therein, and methods of making the same are well known in the art. In one class of embodiments, the water-soluble film includes PVOH. PVOH is a synthetic resin generally prepared by the alcoholysis, usually termed hydrolysis or saponification, of polyvinyl acetate. Fully hydrolyzed PVOH, wherein virtually all the acetate groups have been converted to alcohol groups, is a strongly hydrogen-bonded, highly crystalline polymer which dissolves only in hot water—greater than about 140° F. (60° C.). If a sufficient number of acetate groups are allowed to remain after the hydrolysis of polyvinyl acetate, the PVOH polymer then being known as partially hydrolyzed, it is more weakly hydrogen-bonded and less crystalline and is soluble in cold water—less than about 50° F. (10° C.). An intermediate cold/hot water-soluble film can include, for example, intermediate partially-hydrolyzed PVOH (e.g., with degrees of hydrolysis of about 94% to about 98%), and is readily soluble only in warm water—e.g., rapid dissolution at temperatures of about 40° C. and greater. Both fully and partially hydrolyzed PVOH types are commonly referred to as PVOH homopolymers although the partially hydrolyzed type is technically a vinyl alcohol-vinyl acetate copolymer.

The degree of hydrolysis of the PVOH included in the water-soluble films of the present disclosure can be about 75% to about 99%. As the degree of hydrolysis is reduced, a film made from the resin will have reduced mechanical strength but faster solubility at temperatures below about 20° C. As the degree of hydrolysis increases, a film made from the resin will tend to be mechanically stronger and the thermoformability will tend to decrease. The degree of hydrolysis of the PVOH can be chosen such that the water-solubility of the resin is temperature dependent, and thus the solubility of a film made from the resin, compatibilizing agent, and additional ingredients is also influenced. In one class of embodiments the film is cold water-soluble. A cold water-soluble film, soluble in water at a temperature of less than 10° C., can include PVOH with a degree of hydrolysis in a range of about 75% to about 90%, or in a range of about 80% to about 90%, or in a range of about 85% to about 90%. In another class of embodiments the film is hot water-soluble. A hot water-soluble film, soluble in water at a temperature of at least about 60° C., can include PVOH with a degree of hydrolysis of at least about 98%.

Other film-forming resins for use in addition to or in an alternative to PVOH can include, but are not limited to, modified polyvinyl alcohols, polyacrylates, water-soluble acrylate copolymers, polyacrylates, polyacryamides, polyvinyl pyrrolidone, pullulan, water-soluble natural polymers including, but not limited to, guar gum, xanthan gum, carrageenan, and starch, water-soluble polymer derivatives including, but not limited to, ethoxylated starch and hydroxypropylated starch, poly(sodium acrylamido-2-methylpropane sulfonate), polymonomethylmaleate, copolymers thereof, and combinations of any of the foregoing. In one class of embodiments, the film-forming resin is a terpolymer consisting of vinyl alcohol, vinyl acetate, and sodium acrylamido-2-methylpropanesulfonate. Unexpectedly, water-soluble films based on a vinyl alcohol, vinyl acetate, and sodium acrylamido-2-methylpropanesulfonate terpolymer have demonstrated a high percent recovery of enzyme.

The water-soluble resin can be included in the water-soluble film in any suitable amount, for example an amount in a range of about 35 wt % to about 90 wt %. The preferred weight ratio of the amount of the water-soluble resin as compared to the combined amount of all enzymes, enzyme stabilizers, and secondary additives can be any suitable ratio, for example a ratio in a range of about 0.5 to about 5, or about 1 to 3, or about 1 to 2.

Water-soluble resins for use in the films described herein (including, but not limited to PVOH resins) can be characterized by any suitable viscosity for the desired film properties, optionally a viscosity in a range of about 5.0 to about 30.0 cP, or about 10.0 cP to about 25 cP. The viscosity of a PVOH resin is determined by measuring a freshly made solution using a Brookfield LV type viscometer with UL adapter as described in British Standard EN ISO 15023-2: 2006 Annex E Brookfield Test method. It is international practice to state the viscosity of 4% aqueous polyvinyl alcohol solutions at 20° C. All PVOH viscosities specified herein in cP should be understood to refer to the viscosity of 4% aqueous polyvinyl alcohol solution at 20° C., unless specified otherwise.

It is well known in the art that the viscosity of a PVOH resin is correlated with the weight average molecular weight ($\overline{M}w$) of the same PVOH resin, and often the viscosity is used as a proxy for $\overline{M}w$. Thus, the weight average molecular weight of the water-soluble resin optionally can be in a range of about 35,000 to about 190,000, or about 80,000 to about 160,000. The molecular weight of the resin need only be sufficient to enable it to be molded by suitable techniques to form a thin plastic film.

The water-soluble films according to the present disclosure may include other optional additive ingredients including, but not limited to, plasticizers, surfactants, defoamers, film formers, antiblocking agents, internal release agents, anti-yellowing agents and other functional ingredients, for example in amounts suitable for their intended purpose.

Water is recognized as a very efficient plasticizer for PVOH and other polymers; however, the volatility of water makes its utility limited since polymer films need to have at least some resistance (robustness) to a variety of ambient conditions including low and high relative humidity. Glycerin is much less volatile than water and has been well established as an effective plasticizer for PVOH and other polymers. Glycerin or other such liquid plasticizers by themselves can cause surface "sweating" and greasiness if the level used in the film formulation is too high. This can lead to problems in a film such as unacceptable feel to the hand of the consumer and even blocking of the film on the roll or in stacks of sheets if the sweating is not mitigated in some manner, such as powdering of the surface. This could be characterized as over plasticization. However, if too little plasticizer is added to the film the film may lack sufficient ductility and flexibility for many end uses, for example to be converted into a final use format such as pouches.

Plasticizers for use in water-soluble films of the present disclosure include, but are not limited to, sorbitol, glycerol, diglycerol, propylene glycol, ethylene glycol, diethyleneglycol, triethylene glycol, tetraethyleneglycol, polyethylene glycols up to MW 400, 2 methyl 1,3 propane diol, lactic acid, monoacetin, triacetin, triethyl citrate, 1,3-butanediol, trimethylolpropane (TMP), polyether triol, and combinations thereof. Polyols, as described above, are generally useful as plasticizers. As less plasticizer is used, the film can become more brittle, whereas as more plasticizer is used the film can lose tensile strength. Plasticizers can be included in the water-soluble films in an amount in a range of about 25 phr to about 50 phr, or from about 30 phr to about 45 phr, or from about 32 phr to about 42 phr, for example.

Surfactants for use in water-soluble films are well known in the art. Optionally, surfactants are included to aid in the dispersion of the resin solution upon casting. Suitable surfactants for water-soluble films of the present disclosure include, but are not limited to, dialkyl sulfosuccinates, lactylated fatty acid esters of glycerol and propylene glycol, lactylic esters of fatty acids, sodium alkyl sulfates, polysorbate 20, polysorbate 60, polysorbate 65, polysorbate 80, alkyl polyethylene glycol ethers, lecithin, acetylated fatty acid esters of glycerol and propylene glycol, sodium lauryl sulfate, acetylated esters of fatty acids, myristyl dimethylamine oxide, trimethyl tallow alkyl ammonium chloride, quaternary ammonium compounds, salts thereof and combinations of any of the forgoing. Thus, surfactants can be included in the water-soluble films in an amount of less than about 2 phr, for example less than about 1 phr, or less than about 0.5 phr, for example.

One type of secondary component contemplated for use is a defoamer. Defoamers can aid in coalescing of foam bubbles. Suitable defoamers for use in water-soluble films according to the present disclosure include, but are not limited to, hydrophobic silicas, for example silicon dioxide or fumed silica in fine particle sizes, including Foam Blast® defoamers available from Emerald Performance Materials, including Foam Blast® 327, Foam Blast® UVD, Foam Blast® 163, Foam Blast® 269, Foam Blast® 338, Foam Blast® 290, Foam Blast® 332, Foam Blast® 349, Foam Blast® 550 and Foam Blast® 339, which are proprietary, non-mineral oil defoamers. In embodiments, defoamers can be used in an amount of 0.5 phr, or less, for example, 0.05 phr, 0.04 phr, 0.03 phr, 0.02 phr, or 0.01 phr. Preferably, significant amounts of silicon dioxide will be avoided, in order to avoid stress whitening.

Processes for making water-soluble articles, including films, include casting, blow-molding, extrusion and blown extrusion, as known in the art. One contemplated class of embodiments is characterized by the water-soluble film described herein being formed by casting, for example, by admixing the ingredients described herein with water to create an aqueous mixture, for example a solution with optionally dispersed solids, applying the mixture to a surface, and drying off water to create a film. Similarly, other compositions can be formed by drying the mixture while it is confined in a desired shape.

In one contemplated class of embodiments, the water-soluble film is formed by casting a water-soluble mixture wherein the water-soluble mixture is prepared according to the steps of:
(a) providing a mixture of water-soluble resin, water, and any optional additives excluding plasticizers;
(b) boiling the mixture for 30 minutes;
(c) degassing the mixture in an oven at a temperature of at least 40° C.; optionally in a range of 40° C. to 70° C., e.g., about 65° C.;
(d) adding one or more enzymes, plasticizer, and additional water to the mixture at a temperature of 65° C. or less; and (e) stirring the mixture without vortex until the mixture appears substantially uniform in color and consistency; optionally for a time period in a range of 30 minutes to 90 minutes, optionally at least 1 hour; and (f) casting the mixture promptly after the time period of stirring (e.g., within 4 hours, or 2 hours, or 1 hour).

If the enzyme is added to the mixture too early, e.g., with the secondary additives or resin, the activity of the enzyme may decrease. Without intending to be bound by any particular theory, it is believed that boiling of the mixture with the enzyme leads to the enzyme denaturing and storing in solution for extended periods of time also leads to a reduction in enzyme activity.

In one class of embodiments, high enzyme activity is maintained in the water-soluble films according to the present disclosure by drying the films quickly under moderate to mild conditions. As used herein, drying quickly refers to a drying time of less than 24 hours, optionally less than 12 hours, optionally less than 8 hours, optionally less than 2 hours, optionally less than 1 hour, optionally less than 45 minutes, optionally less than 30 minutes, optionally less than 20 minutes, optionally less than 10 minutes, for example in a range of about 6 minutes to about 10 minutes, or 8 minutes. As used herein, moderate to mild conditions refer to drying temperatures of less than 170° F. (77° C.), optionally in a range of about 150° F. to about 170° F. (about 66° C. to about 77° C.), e.g., 165° F. (74° C.). As the drying temperature increases, the enzymes tend to denature faster, whereas as the drying temperature decreases, the drying time increases, thus exposing the enzymes to solution for an extended period of time.

The film is useful for creating a packet to contain a composition, for example laundry or dishwashing compositions, thereby forming a pouch. The film described herein can also be used to make a packet with two or more compartments made of the same film or in combination with films of other polymeric materials. Additional films can, for example, be obtained by casting, blow-molding, extrusion or blown extrusion of the same or a different polymeric material, as known in the art. In one type of embodiment, the polymers, copolymers or derivatives thereof suitable for use as the additional film are selected from polyvinyl alcohols, polyvinyl pyrrolidone, polyalkylene oxides, polyacrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatin, natural gums such as xanthan, and carrageenans. For example, polymers can be selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and combinations thereof, or selected from polyvinyl alcohols, polyvinyl alcohol copolymers and hydroxypropyl methyl cellulose (HPMC), and combinations thereof.

The pouches and/or packets of the present disclosure comprise at least one sealed compartment. Thus the pouches may comprise a single compartment or multiple compartments. The pouches may have regions with and without enzymes. In embodiments including multiple compartments, each compartment may contain identical and/or different compositions. In turn, the compositions may take any suitable form including, but not limited to liquid, solid and combinations thereof (e.g., a solid suspended in a liquid). In some embodiments, the pouches comprises a first, second and third compartment, each of which respectively contains a different first, second and third composition. In some embodiments, the compositions may be visually distinct as described in EP 2258820.

The compartments of multi-compartment pouches and/or packets may be of the same or different size(s) and/or volume(s). The compartments of the present multi-compartment pouches can be separate or conjoined in any suitable manner. In some embodiments, the second and/or third and/or subsequent compartments are superimposed on the first compartment. In one embodiment, the third compartment may be superimposed on the second compartment, which is in turn superimposed on the first compartment in a sandwich configuration. Alternatively the second and third compartments may be superimposed on the first compartment. However it is also equally envisaged that the first, second and optionally third and subsequent compartments may be attached to one another in a side by side relationship. The compartments may be packed in a string, each compartment being individually separable by a perforation line. Hence each compartment may be individually torn-off from the remainder of the string by the end-user.

In some embodiments, multi-compartment pouches and/or packets include three compartments consisting of a large first compartment and two smaller compartments. The second and third smaller compartments are superimposed on the first larger compartment. The size and geometry of the compartments are chosen such that this arrangement is achievable. The geometry of the compartments may be the same or different. In some embodiments the second and optionally third compartment each has a different geometry and shape as compared to the first compartment. In these embodiments, the second and optionally third compartments are arranged in a design on the first compartment. The design may be decorative, educative, or illustrative, for example to illustrate a concept or instruction, and/or used to indicate origin of the product. In some embodiments, the first compartment is the largest compartment having two large faces sealed around the perimeter, and the second compartment is smaller covering less than about 75%, or less than about 50% of the surface area of one face of the first compartment. In embodiments in which there is a third compartment, the aforementioned structure may be the same but the second and third compartments cover less than about 60%, or less than about 50%, or less than about 45% of the surface area of one face of the first compartment.

The pouches and/or packets of the present disclosure may comprise one or more different films. For example, in single compartment embodiments, the packet may be made from one wall that is folded onto itself and sealed at the edges, or alternatively, two walls that are sealed together at the edges. In multiple compartment embodiments, the packet may be made from one or more films such that any given packet compartment may comprise walls made from a single film or multiple films having differing compositions. In one embodiment, a multi-compartment pouch comprises at least three walls: an outer upper wall; an outer lower wall; and a partitioning wall. The outer upper wall and the outer lower wall are generally opposing and form the exterior of the pouch. The partitioning wall is interior to the pouch and is secured to the generally opposing outer walls along a seal line. The partitioning wall separates the interior of the multi-compartment pouch into at least a first compartment and a second compartment. In one class of embodiments, the partitioning wall may be the only enzyme containing film thereby minimizing the exposure of the consumer to the enzymes.

Pouches and packets may be made using any suitable equipment and method. For example, single compartment pouches may be made using vertical form filling, horizontal form filling, or rotary drum filling techniques commonly known in the art. Such processes may be either continuous or intermittent. The film may be dampened, and/or heated to increase the malleability thereof. The method may also involve the use of a vacuum to draw the film into a suitable mold. The vacuum drawing the film into the mold can be applied for about 0.2 to about 5 seconds, or about 0.3 to about 3, or about 0.5 to about 1.5 seconds, once the film is on the horizontal portion of the surface. This vacuum can be such that it provides an under-pressure in a range of 10 mbar to 1000 mbar, or in a range of 100 mbar to 600 mbar, for example.

The molds, in which packets may be made, can have any shape, length, width and depth, depending on the required dimensions of the pouches. The molds may also vary in size and shape from one to another, if desirable. For example, the volume of the final pouches may be about 5 ml to about 300 ml, or about 10 to 150 ml, or about 20 to about 100 ml, and that the mold sizes are adjusted accordingly.

In one embodiment, the packet includes a first and a second sealed compartment. The second compartment is in a generally superposed relationship with the first sealed compartment such that the second sealed compartment and the first sealed compartment share a partitioning wall interior to the pouch.

In one embodiment, the packet including a first and a second compartment further includes a third sealed compartment. The third sealed compartment is in a generally superposed relationship with the first sealed compartment such that the third sealed compartment and the first sealed compartment share a partitioning wall interior to the pouch.

In various embodiments, the first composition and the second composition are selected from one of the following combinations: liquid, liquid; liquid, powder; powder, powder; and powder, liquid.

In various embodiments, the first, second and third compositions are selected from one of the following combinations: solid, liquid, liquid and liquid, liquid, liquid.

In one embodiment, the single compartment or plurality of sealed compartments contains a composition. The plurality of compartments may each contain the same or a different composition. The composition is selected from a liquid, solid or combination thereof.

Heat can be applied to the film in the process commonly known as thermoforming. The heat may be applied using any suitable means. For example, the film may be heated directly by passing it under a heating element or through hot air, prior to feeding it onto a surface or once on a surface. Alternatively, it may be heated indirectly, for example by heating the surface or applying a hot item onto the film. The film can be heated using an infrared light. The film may be heated to a temperature of at least 50° C., for example about 50 to about 150° C., about 50 to about 120° C., about 60 to about 130° C., about 70 to about 120° C., or about 60 to about 90° C.

Alternatively, the film can be wetted by any suitable means, for example directly by spraying a wetting agent (including water, a solution of the film composition, a plasticizer for the film composition, or any combination of the foregoing) onto the film, prior to feeding it onto the surface or once on the surface, or indirectly by wetting the surface or by applying a wet item onto the film.

Once a film has been heated and/or wetted, it may be drawn into an appropriate mold, preferably using a vacuum. The film can be thermoformed with a draw ratio of at least about 1.5, for example, and optionally up to a draw ratio of 2, for example. The filling of the molded film can be accomplished by utilizing any suitable means. In some embodiments, the most preferred method will depend on the product form and required speed of filling. In some embodiments, the molded film is filled by in-line filling techniques. The filled, open packets are then closed forming the pouches, using a second film, by any suitable method. This may be accomplished while in horizontal position and in continuous, constant motion. The closing may be accomplished by continuously feeding a second film, preferably water-soluble film, over and onto the open packets and then preferably sealing the first and second film together, typically in the area between the molds and thus between the packets.

Any suitable method of sealing the packet and/or the individual compartments thereof may be utilized. Non-limiting examples of such means include heat sealing, solvent welding, solvent or wet sealing, and combinations thereof. The water-soluble packet and/or the individual compartments thereof can be heat sealed at a temperature of at least 200° F. (93° C.), for example in a range of about 220° F. (about 105° C.) to about 290° F. (about 145° C.), or about 230° F. (about 110° C.) to about 280° F. (about 140° C.). Typically, only the area which is to form the seal is treated with heat or solvent. The heat or solvent can be applied by any method, typically on the closing material, and typically only on the areas which are to form the seal. If solvent or wet sealing or welding is used, it may be preferred that heat is also applied. Preferred wet or solvent sealing/welding methods include selectively applying solvent onto the area between the molds, or on the closing material, by for example, spraying or printing this onto these areas, and then applying pressure onto these areas, to form the seal. Sealing rolls and belts as described above (optionally also providing heat) can be used, for example.

The formed pouches may then be cut by a cutting device. Cutting can be accomplished using any known method. It may be preferred that the cutting is also done in continuous manner, and preferably with constant speed and preferably while in horizontal position. The cutting device can, for example, be a sharp item, or a hot item, or a laser, whereby in the latter cases, the hot item or laser 'burns' through the film/sealing area.

The different compartments of a multi-compartment pouches may be made together in a side-by-side style wherein the resulting, cojoined pouches may or may not be separated by cutting. Alternatively, the compartments can be made separately.

In some embodiments, pouches may be made according to a process including the steps of:
a) forming a first compartment (as described above);
b) forming a recess within some or all of the closed compartment formed in step (a), to generate a second molded compartment superposed above the first compartment;
c) filling and closing the second compartments by means of a third film;
d) sealing the first, second and third films; and
e) cutting the films to produce a multi-compartment pouch.

The recess formed in step (b) may be achieved by applying a vacuum to the compartment prepared in step (a).

In some embodiments, second, and/or third compartment(s) can be made in a separate step and then combined with the first compartment as described in EP 2088187 or WO 2009/152031.

In other embodiments, pouches may be made according to a process including the steps of:
a) forming a first compartment, optionally using heat and/or vacuum, using a first film on a first forming machine;
b) filling the first compartment with a first composition;
c) on a second forming machine, deforming a second film, optionally using heat and vacuum, to make a second and optionally third molded compartment;
d) filling the second and optionally third compartments;
e) sealing the second and optionally third compartment using a third film;
f) placing the sealed second and optionally third compartments onto the first compartment;
g) sealing the first, second and optionally third compartments; and
h) cutting the films to produce a multi-compartment pouch.

The first and second forming machines may be selected based on their suitability to perform the above process. In some embodiments, the first forming machine is preferably a horizontal forming machine, and the second forming machine is preferably a rotary drum forming machine, preferably located above the first forming machine.

It should be understood that by the use of appropriate feed stations, it may be possible to manufacture multi-compartment pouches incorporating a number of different or distinctive compositions and/or different or distinctive liquid, gel or paste compositions.

Lipase prepared according to the method may be activated or reactivated upon contact with detergent and/or protease. In some aspects the present invention relates to a method for increasing the activity of the lipase prepared according to the method, comprising the step of bringing said lipase into contact with protease and/or detergent.

EXAMPLES

Materials

Chemicals used as buffers and substrates were commercial products of at least reagent grade unless otherwise noted.

Example 1

Expression and Purification of RmL and RmL Propeptide

The gene of *Rhizomucor miehei* lipase (RmL) SEQ ID No: 1 was cloned into the expression vector, pENI2516 and transformed in the expression host, *Aspergillus oryzae* ToC1512.

SEQ ID No: 1 sets forth the nucleotide sequence of the RmL including the sequence encoding the prepropeptide (underligned) cleaved of:

<u>atg gtt ctc aag cag cgt gca aac tac</u>

<u>cta gga ttt ctg att gta ttc ttc</u>

<u>acg gcc ttc ctg gtg gaa gcg gta ccc</u>

<u>atc aag aga caa tcg aat tcc acg</u>

<u>gtc gac agt ctg ccg cct ctc atc ccc</u>

<u>tcg aga acc tcg gca cct tca tca</u>

<u>tca cca agc aca acc gac cct gaa gct</u>

-continued

<u>cca gcc atg agt cgc aat gga ccg</u>

<u>ctg ccc tcg gat gta gag act aaa tat</u>

<u>ggc atg gct ttg aat gct act tcc</u>

<u>tat ccg gat tct gtg gtc caa gca atg</u> agc att gat ggt ggt atc cgc gct gcg acc tcg caa gaa atc aat gaa ttg act tat tac act aca cta tct gcc aac tcg tac tgc cgc act gtc att cct gga gct acc tgg gac tgt atc cac tgt gat gca acg gag gat ctc aag att atc aag act tgg agc acg ctc atc tat gat aca aat gca atg gtt gca cgt ggt gac agc gaa aaa act atc tat atc gtt ttc cga ggt tcg agc tct atc cgc aac tgg att gct gat ctc acc ttt gtg cca gtt tca tat cct ccg gtc agt ggt aca aaa gta cac aag gga ttc ctg gac agt tac ggg gaa gtt caa aac gag ctt gtt gct act gtt ctt gat caa ttc aag caa tat cca agc tac aag gtt gct gtt aca ggt cac tca ctc ggt ggt gct act gcg ttg ctt tgc gcc ctg gat ctc tat caa cga gaa gaa gga ctc tca tcc agc aac ttg ttc ctt tac act caa ggt caa cca cgg gta ggc gac cct gcc ttt gcc aac tac gtt gtt agc acc ggc att cct tac agg cgc acg gtc aat gaa cga gat atc gtt cct cat ctt cca cct gct gct ttt ggt ttt ctc cac gct ggc gag gag tat tgg att act gac aat agc cca gag act gtt cag gtc tgc aca agc gat ctg gaa acc tct gat tgc tct aac agc att gtt ccc ttc aca agt gtt ctt gac cat ctc tcg tac ttt Asn Ser Ile Val Pro Phe Thr Ser Val Leu Asp His Leu Ser Tyr Phe ggt atc aac aca ggc ctc tgt act SEQ ID No: 2 sets forth the amino acid sequence of the RmL including the preprosequence (underligned) cleaved of:

```
MVLKQRANYL GFLIVFFTAF LVEAVPIKRQ

SNSTVDSLPP LIPSRTSAPS SSPSTTDPEA

PAMSRNGPLP SDVETKYGMA LNATSYPDSV

VQAMSIDGGI RAATSQEINE LTYYTTLSAN

SYCRTVIPGA TWDCIHCDAT EDLKIIKTWS

TLIYDTNAMV ARGDSEKTIY IVFRGSSSIR

NWIADLTFVP VSYPPVSGTK VHKGFLDSYG

EVQNELVATV LDQFKQYPSY KVAVTGHSLG

GATALLCALD LYQREEGLSS SNLFLYTQGQ

PRVGDPAFAN YVVSTGIPYR RTVNERDIVP

HLPPAAFGFL HAGEEYWITD NSPETVQVCT

SDLETSDCSN SIVPFTSVLD HLSYFGINTG LCT
```

SEQ ID No: 3 sets forth the amino acid sequence of the RmL mature protein:

```
SIDGGIRAAT SQEINELTYY TTLSANSYCR

TVIPGATWDC IHCDATEDLK IIKTWSTLIY

DTNAMVARGD SEKTIYIVFR GSSSIRNWIA

DLTFVPVSYP PVSGTKVHKG FLDSYGEVQN

ELVATVLDQF KQYPSYKVAV TGHSLGGATA

LLCALDLYQR EEGLSSSNLF LYTQGQPRVG

DPAFANYVVS TGIPYRRTVN ERDIVPHLPP

AAFGFLHAGE EYWITDNSPE TVQVCTSDLE

TSDCSNSIVP FTSVLDHLSY FGINTGLCT
```

SEQ ID No: 4 sets forth the amino acid sequence of the propeptide of RmL:

```
VPIKRQSNST VDSLPPLIPS RTSAPSSSPS TTDPEAPAMS
RNGPLPSDVE TKYGMALNAT SYPDSVVQAM
```

Purification of RmL

Culture supernatant from *Aspergillus oryzae* broth was filtered through PES Bottle top filter with a 0.22 um cut-off. The resulting filtrate was mixed 1:1 with 50 mM Hepes pH7, 2M NaCl and if necessary further pH adjusted to pH7.

The pretreated sample was purified by HIC/affinity chromatography on approximately 50 mL Decylamine agarose. During the application the flow-through was collected as the pool of lipase not binding to the decylamine column and having the pro-peptide bound. After 3 column volumes (CV) wash with Buffer A (50 mM Hepes; pH7+1M NaCl), the lipase (without pro-peptide) bound to the column was eluted in a step-gradient of 3CV 100% buffer B (MilliQ water).

Gelfiltration of Rml with and Without Pro-Peptide 200 uL of Rml with and without pro-peptide were loaded on to Superdex200 10/300 GL gel filtration column with a flow of 0.5 mL/min. The mobile phase was 10 mM Hepes pH7, 300 mM NaCl. The column was calibrated with the LMW Gel filtration calibration kit (product code 28-4038-41, GE Healthcare Europe GmbH, Park Allé 295, 2605 Brondby, Denmark,) and a linear relationship between the retention time and the molecular weight was established according to the kit manual. The retention time of the RmL is 16.9 min, which corresponds to a molecular weight of 27 kD. The retention time of RmL with propeptide bound is 15.9 min, which correspond to a molecular weight of 42 kD.

Detection of RmL N-Terminal Fragment

Protein identification was performed by tandem mass spectrometry (MS/MS) analysis of peptides released by protease digestion. For this the purified samples of RmL were first TCA precipitated. The protein pellet was solubilized in a Guanidine-HCL denaturation buffer that was heated with DTT for reduction of disulfide bonds followed by alkylation with Iodoaceamide. The samples were then washed and digested with a specific protease like trypsin on a 10 kDa cut-off filter membrane. Following digestion the generated tryptic peptides were extracted and analyzed on an Orbitrap LTQ Velos Pro mass spectrometer (Thermo Scientific) where peptide masses and peptide fragment masses are measured.

For protein identification the experimentally obtained masses were compared with the theoretical peptide masses and peptide fragment masses of proteins stored in databases by the mass search program Mascot (Matrix science). In addition to the mature protein sequence the data showed significant sequence coverage of the N-terminal propeptide corresponding to amino acid −70 to −1 of SEQ ID NO: 2.

The association of the propeptide to the mature protein of the lipase is non-covalent. This was concluded from analysis of the same RmL samples on a denaturing SDS page where only a protein band corresponding to the RmL without propeptide could be identified.

Purification of the RmL Propeptide

The RmL propeptide was separated from RmL in a 2-step purification process at a pH at approximately 2.0-2.5. The starting material (unbound fraction from a hydrophobic interaction purification of the lipase) was diluted 20-fold in 10% w/w EtOH, 1% w/w formic acid and applied on a C8-silica resin (SP-200-15-C8-HP from Daiso Co. Ltd). The column was washed with 10% w/w EtOH, 1% w/w formic acid and the peptide eluted as a very broad product peak with a linear gradient from 10% w/w EtOH, 1% w/w formic acid to 50% w/w EtOH, 1% w/w formic acid. RmL-propeptide containing fractions as identified by peptide mapping by MS were combined and diluted 10-fold in dH$_2$O and applied on a C5-silica resin (C5 Jupiter® 10 um, 300 Å from Phenomenex). The column was washed with 10% w/w EtOH, 1% w/w formic acid and the peptide eluted as a broad product peak with a linear gradient from 10% w/w EtOH, 1% w/w formic acid to 50% w/w EtOH, 1% w/w formic acid. RML-propeptide containing fractions as identified by peptide mapping by MS were combined and dried in a centrifugal evaporator at room temperature. The dried material was dissolved in 50 mM Na-acetate pH4.

Example 2

The Effect of Propeptide on Hydrolytic Activity on Fatty Acids

The hydrolytic activity of RmL with and without propeptide on various fatty acids was investigated in a kinetic assay using p-nitrophenyl acyl esters as substrate. The 100 mM stock solutions in DMSO of the substrates: p-Nitrophenyl butyrate (C3), p-Nitrophenyl caproate (C6), p-Nitrophenyl caprate (C10), p-Nitrophenyl laurate (C12) and p-Nitrophenyl palmitate (C16) (all from Sigma-Aldrich Danmark A/S, Kirkebjerg Allé 84, 2605 Brøndby; Cat.no.: C3:N-9876, C6: N-0502, C10: N-0252, C12: N-2002, C16: N-2752) were diluted to a final concentration of 1 mM into assay buffer (50 mM Tris; pH 7.7; 0.4% TritonX-100).

RmL with and without propeptide and appropriate controls: Buffer (negative), Lipex™ (positive) RmL with and without propeptide in 50 mM Hepes pH8.0; 10 ppm TritonX-100; 20 mM $CaCl_2$ were added to the substrate solution in the following final concentrations: 0.01 mg/mL; $5 \times 10^{-3}$ mg/mL; $2.5 \times 10^{-4}$ mg/mL; and $1.25 \times 10^{-4}$ mg/mL in 96-well NUNC plates (Cat. No: 260836, Kamstrupvej 90, DK-4000, Roskilde). Release of p-nitrophenol by hydrolysis of p-nitrophenyl acyl was monitored at 405 nm for 5 minutes in 10 second intervals on a Spectra max 190 (Molecular Devices GmbH, Bismarckring 39, 88400 Biberach an der Riss, GERMANY).

RmL showed activity in all conditions tested with a maximal activity at C10. RmL with the propeptide bound showed no activity at any of the conditions tested.

Example 3

Determination of Td by Differential Scanning Calorimetry

The thermostability of *Rhizomucor miehei* lipase, RmL (SEQ ID NO: 3) with or without non covalently bound native propeptide (SEQ ID NO: 4) was determined by Differential Scanning calorimetry (DSC) using a VP-Capillary Differential Scanning calorimeter (MicroCal Inc., Piscataway, N.J., USA).

The thermal denaturation temperature, Td (° C.), was taken as the top of denaturation peak (major endothermic peak) in thermograms (Cp vs. T) obtained after heating enzyme solutions in buffer (50 mM HEPES; 100 mM NaCl; 1 mM CaCl2; pH8.0) at a constant programmed heating rate of 200 K/hr. RmL without propeptide added was analyzed at a concentration of 0.42 mg/mL, where as in presence of propeptide the concentration of RmL was 0.34 mg/mL as a consequence of mixing of 440 uL enzyme solution (at 0.42 mg/mL) and 100 uL peptid solution at a concentration of 480 uM (concentration determined by amino acid analysis).

Sample- and reference-solutions (approx. 0.2 mL) were loaded into the calorimeter (reference: buffer without enzyme) from storage conditions for 3 hours (mixing) at 10° C. and thermally pre-equilibrated for approx. 20 minutes at 20° C. prior to DSC scan from 20° C. to 100° C. Denaturation temperatures were determined at an accuracy of approximately +/−1° C.

TABLE 1

| Thermostability | |
|---|---|
| | Td at pH 8.0 |
| RmL | 61° C. |
| RmL + peptide | 68° C. |

Example 4

Automatic Mechanical Stress Assay (AMSA

Washing experiments were performed using Automatic Mechanical Stress Assay (AMSA) in order to assess the wash performance in laundry. The AMSA plate has a number of slots for test solutions and a lid firmly squeezing the laundry sample, the textile to be washed against all the slot openings. During the washing time, the plate, test solutions, textile and lid were vigorously shaken to bring the test solution in contact with the textile and apply mechanical stress in a regular, periodic oscillating manner. For further description see WO02/42740 especially the paragraph "Special method embodiments" at page 23-24.

The laundry experiments were conducted in Model Detergent B, pH8. The experimental conditions are specified below:

| | |
|---|---|
| Concentration of Detergents/buffers: | 3.3 g/L Detergent 60% surfactant, 50 mM glycine buffer pH 8 |
| Test solution volume: | 160 uL |
| Wash time: | 15 minutes |
| Temperature: | 25° C. |
| Water hardness: | 15° dH |
| Lipase dosage: | 0 ppm or 0.5 ppm |
| Test material: | Cream turmeric stain according to WO06/125437 |

| Ingredient | Amount (wt %) |
|---|---|
| NaOH, pellets (>99%) | 1.05 |
| Linear alkylbenzenesulfonic acid (LAS) (97%) | 7.20 |
| Sodium laureth sulfate (SLES) (28%) | 10.58 |
| Soy fatty acid (>90%) | 2.75 |
| Coco fatty acid (>99%) | 2.75 |
| AEO; alcohol ethoxylate with 8 mol EO; Lutensol TO 8 (~100%) | 6.60 |
| Triethanol amine (100%) | 3.33 |
| Na-citrate, dihydrate (100%) | 2.00 |
| DTMPA; diethylenetriaminepentakis(methylene)pentakis(phosphonic acid), heptasodium salt (Dequest 2066 C) (~42% as Na7 salt) | 0.48 |
| MPG (>98%) | 6.00 |
| EtOH, propan-2-ol (90/10%) | 3.00 |
| Glycerol (>99.5) | 1.71 |
| Sodium formate (>95%) | 1.00 |
| PCA (40% as sodium salt) | 0.46 |
| Water up to | 100 |

Final adjustments to the specified pH were done with NaOH or citric acid. Water hardness was adjusted to 15° dH by addition of $CaCl_2$ and $MgCl_2$ ($Ca^{2+}$:$Mg^{2+}$=4:1) to the test system.

After washing the textiles were flushed in tap water and excess water was removed from the textiles using filter paper and immediately thereafter the textiles were dried at 85° C. for 5 min.

The wash performance was measured as the color change of the washed soiled textile. The soil was cream mixed with turmeric. Turmeric contains the colorant curcumin, which function as a pH indicator by having pH dependent color change. Lipase activity leads to release of free fatty acids from the cream acylglycerides and this leads to pH decrease and thereby color change of the curcumin pH indicator. Lipase wash performance can therefore be expressed as the extent of color change of light reflected-emitted from the washed soiled textile when illuminated with white light.

Color measurements were made with a professional flatbed scanner (EPSON EXPRESSION 10000XL, Atea A/S, Lautrupvang 6, 2750 Ballerup, Denmark), which was used to capture an image of the washed soiled textile. To extract a value for the light intensity from the scanned images, 24-bit pixel values from the image were converted into values for red, green and blue (RGB).

Color change due to lipase activity was measured as the increase in the reflection-emitting of green light (G) relative to the sum of reflected-emitted blue (B) and red (R) light. The wash performance (RP(Wash)) of a lipase relative to a reference lipase (Lipolase™) was calculated as: RP(Wash)=(G/(B+R)(tested lipase)−G/(B+R)(no enzyme))/(G/(B+R)(lipase ref.)−G/(B+R)(no enzyme)).

Example 5

Inhibitory Effect of Propeptide

The inhibitory effect of the isolated propeptide (PP) was determined by mixing isolated propeptide in molar excess with separately purified active RmL core-enzyme at increasing molar ratios of propeptide to lipase. RmL was diluted in 10 mM succinic acid buffer, pH6.5, to a concentration of 1.5 uM and mixed (1:1) with purified propeptide diluted in 10 mM succinic acid buffer, pH6.5 to give the final molar ratios in the mix as listed below. After 3 hours incubation at 4° C. lipase wash performance of the incubated lipase-inhibitor samples were determined by Automatic Mechanical Stress Assay (AMSA) as described above. The reproducibility is shown by four repetitions within the same swatch. The relative wash performance (RP) is for each repetition normalized to the wash performance of without inhibitor.

TABLE 2

Propeptide dose response

Detergent: Model B/50 mM glycine pH 8

| RP(wash) | Rep. 1 | Rep. 2 | Rep. 3 | Rep. 4 |
|---|---|---|---|---|
| RmL without PP | 1.00 | 1.00 | 1.00 | 1.00 |
| RmL 1:3 PP | 0.62 | 0.78 | 0.62 | 0.67 |
| RmL 1:6 PP | 0.65 | 0.65 | 0.51 | 0.57 |
| RmL 1:60 PP | 0.18 | 0.18 | 0.18 | 0.06 |
| RmL 1:320 PP | −0.03 | −0.02 | −0.05 | −0.06 |

Example 6

Specificity of Inhibitory Effect of Propeptide

The inhibitory specificity of the isolated propeptide was determined by mixing the isolated propeptide in a 320:1 molar ratio with 5 different lipases including the active RmL. All enzymes were diluted in 10 mM succinic acid buffer, pH6.5, to a concentration of 1.5 uM and were mixed (1:1) with purified propeptide dilutions. After 3 hours incubation at 4° C. the lipase performance of the incubated lipase-inhibitor samples were determined by Automatic Mechanical Stress Assay (AMSA) as described above. The relative wash performance "RP(wash)" is for each lipase normalized to the wash performance without inhibitor. The inhibitor shows exclusively effect with RmL.

TABLE 3

Effect of inhibition with SEQ ID No: 4

| Enzyme | No inhibitor RP(wash) | With inhibitor RP(wash) |
|---|---|---|
| SEQ ID NO: 3 (RmL* without propeptide) | 1.00 | 0.02 |
| SEQ ID NO: 5 (Lipex) | 1.00 | 0.89 |
| SEQ ID NO: 6 (MuciLip2CN) | 1.00 | 1.10 |
| SEQ ID NO: 7 (RhimiLip1) | 1.00 | 0.92 |

Example 7

Activation with Detergent and/or Protease

Wild type RmL without or with propeptide respectively were submitted to no, detergent, protease or detergent+protease treatment prior to performance test in AMSA to test the activation level of the lipase after the treatment. The lipase samples were treated for 60 minutes in 10 mM succinic acid pH6.5, ("No"); 77% (w/w) Model detergent B ("Det"); 1.35% (v/v) Savinase® in 10 mM succinic acid pH6.5 ("Sav"); 1.35% (v/v) Savinase® in 77% (w/w) Detergent B ("Det+Sav"). Wash performance of RmL with propeptide (inactive RmL) was measured after both 10 and 60 minutes of incubation. A full activation was reached with Savinase® treatment in detergent already after 10 minutes. Wash performance of all samples were determined by Automatic Mechanical Stress Assay (AMSA) as described above.

TABLE 4

Activation with detergent and/or protease

| Enzyme | Time (Minutes) | No (RP) | Det (RP) | Sav (RP) | Det + Sav (RP) |
|---|---|---|---|---|---|
| RmL without propeptide | 60 | 1.00 | 0.89 | 0.99 | 0.84 |
| RmL with propeptide | 60 | 0.18 | 0.69 | 0.39 | 0.85 |
| RmL with propeptide | 10 | — | 0.60 | 0.27 | 0.88 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A method for modifying the stability, activity, or wash performance of a parent lipase, comprising non-covalently associating a peptide to the parent lipase to produce a modified lipase;
where the parent lipase has at least 90% sequence identity with amino acids 1 to 269 of SEQ ID NO: 2;
where the peptide has at least 90% sequence identity with the amino acid sequence of at least one major lipase contact zone of the propeptide of the parent lipase; and
where the major lipase contact zone of the propeptide corresponds to any of amino acids −57 to −50; −40 to −28; and −22 to −15 of SEQ ID NO: 2,
wherein the modified lipase has increased thermostability in a detergent as compared to the parent lipase, has decreased lipid stain removal activity as compared to the parent lipase, and/or has increased lipid stain removal activity after contact with a detergent or a protease as compared to the parent lipase.

2. The method of claim 1, comprising formulating the modified lipase into lipase crystals, lipase precipitates, freeze-dried lipase, spray-dried lipase, or granulated lipase.

3. The method of claim 1, comprising bringing the modified lipase into contact with a protease or detergent.

4. The method of claim 1, comprising adding the modified lipase to a detergent composition.

5. The method of claim 4, comprising adding the detergent composition containing the modified lipase to a wash.

6. The method of claim 1, wherein the lipase has at least 95% sequence identity with amino acid 1 to 269 of SEQ ID NO: 2.

7. The method of claim 1, wherein the lipase has at least 96% sequence identity with amino acid 1 to 269 of SEQ ID NO: 2.

8. The method of claim 1, wherein the lipase has at least 97% sequence identity with amino acid 1 to 269 of SEQ ID NO: 2.

9. The method of claim 1, wherein the lipase has at least 98% sequence identity with amino acid 1 to 269 of SEQ ID NO: 2.

10. The method of claim 1, wherein the lipase has at least 99% sequence identity with amino acid 1 to 269 of SEQ ID NO: 2.

* * * * *

SEQUENCE LISTING

<160> NUMBER OF SEQ ID NOS: 8

<210> SEQ ID NO 1
<211> LENGTH: 1110
<212> TYPE: DNA
<213> ORGANISM: Rhizomucor miehei

```
<220> FEATURE:
<221> NAME/KEY: CDS
<222> LOCATION: (13)..(1101)
<220> FEATURE:
<221> NAME/KEY: sig_peptide
<222> LOCATION: (13)..(84)
<220> FEATURE:
<221> NAME/KEY: misc_feature
<222> LOCATION: (85)..(294)
<220> FEATURE:
<221> NAME/KEY: mat_peptide
<222> LOCATION: (295)..(930)

<400> SEQUENCE: 1
```

| | | | | | | | | | | | | | |
|---|---|---|---|---|---|---|---|---|---|---|---|---|---|
| ggatccttca cc | atg | gtt | ctc | aag | cag | cgt | gca | aac | tac | cta | gga | ttt ctg | 51 |
| | Met | Val | Leu | Lys | Gln | Arg | Ala | Asn | Tyr | Leu | Gly | Phe Leu | |
| | | | | -90 | | | | | -85 | | | | |
| att | gta | ttc | ttc | acg | gcc | ttc | ctg | gtg | gaa | gcg | gta | ccc atc aag aga | 99 |
| Ile | Val | Phe | Phe | Thr | Ala | Phe | Leu | Val | Glu | Ala | Val | Pro Ile Lys Arg | |
| | -80 | | | | -75 | | | | | -70 | | | |
| caa | tcg | aat | tcc | acg | gtc | gac | agt | ctg | ccg | cct | ctc | atc ccc tcg aga | 147 |
| Gln | Ser | Asn | Ser | Thr | Val | Asp | Ser | Leu | Pro | Pro | Leu | Ile Pro Ser Arg | |
| -65 | | | | | -60 | | | | | -55 | | | -50 |
| acc | tcg | gca | cct | tca | tca | tca | cca | agc | aca | acc | gac | cct gaa gct cca | 195 |
| Thr | Ser | Ala | Pro | Ser | Ser | Ser | Pro | Ser | Thr | Thr | Asp | Pro Glu Ala Pro | |
| | | | -45 | | | | | -40 | | | | | -35 |
| gcc | atg | agt | cgc | aat | gga | ccg | ctg | ccc | tcg | gat | gta | gag act aaa tat | 243 |
| Ala | Met | Ser | Arg | Asn | Gly | Pro | Leu | Pro | Ser | Asp | Val | Glu Thr Lys Tyr | |
| | | -30 | | | | | -25 | | | | | -20 | |
| ggc | atg | gct | ttg | aat | gct | act | tcc | tat | ccg | gat | tct | gtg gtc caa gca | 291 |
| Gly | Met | Ala | Leu | Asn | Ala | Thr | Ser | Tyr | Pro | Asp | Ser | Val Val Gln Ala | |
| | | -15 | | | | | -10 | | | | | -5 | |
| atg | agc | att | gat | ggt | ggt | atc | cgc | gct | gcg | acc | tcg | caa gaa atc aat | 339 |
| Met | Ser | Ile | Asp | Gly | Gly | Ile | Arg | Ala | Ala | Thr | Ser | Gln Glu Ile Asn | |
| -1 | 1 | | | | 5 | | | | | 10 | | | 15 |
| gaa | ttg | act | tat | tac | act | aca | cta | tct | gcc | aac | tcg | tac tgc cgc act | 387 |
| Glu | Leu | Thr | Tyr | Tyr | Thr | Thr | Leu | Ser | Ala | Asn | Ser | Tyr Cys Arg Thr | |
| | | | 20 | | | | | 25 | | | | | 30 |
| gtc | att | cct | gga | gct | acc | tgg | gac | tgt | atc | cac | tgt | gat gca acg gag | 435 |
| Val | Ile | Pro | Gly | Ala | Thr | Trp | Asp | Cys | Ile | His | Cys | Asp Ala Thr Glu | |
| | | | 35 | | | | | 40 | | | | | 45 |
| gat | ctc | aag | att | atc | aag | act | tgg | agc | acg | ctc | atc | tat gat aca aat | 483 |
| Asp | Leu | Lys | Ile | Ile | Lys | Thr | Trp | Ser | Thr | Leu | Ile | Tyr Asp Thr Asn | |
| | | | 50 | | | | | 55 | | | | | 60 |
| gca | atg | gtt | gca | cgt | ggt | gac | agc | gaa | aaa | act | atc | tat atc gtt ttc | 531 |
| Ala | Met | Val | Ala | Arg | Gly | Asp | Ser | Glu | Lys | Thr | Ile | Tyr Ile Val Phe | |
| | 65 | | | | | 70 | | | | | 75 | | |
| cga | ggt | tcg | agc | tct | atc | cgc | aac | tgg | att | gct | gat | ctc acc ttt gtg | 579 |
| Arg | Gly | Ser | Ser | Ser | Ile | Arg | Asn | Trp | Ile | Ala | Asp | Leu Thr Phe Val | |
| 80 | | | | | 85 | | | | | 90 | | | 95 |
| cca | gtt | tca | tat | cct | ccg | gtc | agt | ggt | aca | aaa | gta | cac aag gga ttc | 627 |
| Pro | Val | Ser | Tyr | Pro | Pro | Val | Ser | Gly | Thr | Lys | Val | His Lys Gly Phe | |
| | | | 100 | | | | | 105 | | | | | 110 |
| ctg | gac | agt | tac | ggg | gaa | gtt | caa | aac | gag | ctt | gtt | gct act gtt ctt | 675 |
| Leu | Asp | Ser | Tyr | Gly | Glu | Val | Gln | Asn | Glu | Leu | Val | Ala Thr Val Leu | |
| | | | 115 | | | | | 120 | | | | | 125 |
| gat | caa | ttc | aag | caa | tat | cca | agc | tac | aag | gtt | gct | gtt aca ggt cac | 723 |
| Asp | Gln | Phe | Lys | Gln | Tyr | Pro | Ser | Tyr | Lys | Val | Ala | Val Thr Gly His | |
| | | | 130 | | | | | 135 | | | | | 140 |
| tca | ctc | ggt | ggt | gct | act | gcg | ttg | ctt | tgc | gcc | ctg | gat ctc tat caa | 771 |
| Ser | Leu | Gly | Gly | Ala | Thr | Ala | Leu | Leu | Cys | Ala | Leu | Asp Leu Tyr Gln | |
| | 145 | | | | | 150 | | | | | 155 | | |

```
cga gaa gaa gga ctc tca tcc agc aac ttg ttc ctt tac act caa ggt    819
Arg Glu Glu Gly Leu Ser Ser Ser Asn Leu Phe Leu Tyr Thr Gln Gly
160             165                 170                 175 caa cca cgg gta ggc gac cct gcc ttt gcc aac tac gtt gtt agc acc    867
Gln Pro Arg Val Gly Asp Pro Ala Phe Ala Asn Tyr Val Val Ser Thr
                180                 185                 190 ggc att cct tac agg cgc acg gtc aat gaa cga gat atc gtt cct cat    915
Gly Ile Pro Tyr Arg Arg Thr Val Asn Glu Arg Asp Ile Val Pro His
            195                 200                 205 ctt cca cct gct gct ttt ggt ttt ctc cac gct ggc gag gag tat tgg    963
Leu Pro Pro Ala Ala Phe Gly Phe Leu His Ala Gly Glu Glu Tyr Trp
        210                 215                 220 att act gac aat agc cca gag act gtt cag gtc tgc aca agc gat ctg   1011
Ile Thr Asp Asn Ser Pro Glu Thr Val Gln Val Cys Thr Ser Asp Leu
225                 230                 235 gaa acc tct gat tgc tct aac agc att gtt ccc ttc aca agt gtt ctt   1059
Glu Thr Ser Asp Cys Ser Asn Ser Ile Val Pro Phe Thr Ser Val Leu
240                 245                 250                 255 gac cat ctc tcg tac ttt ggt atc aac aca ggc ctc tgt act taactcgag 1110
Asp His Leu Ser Tyr Phe Gly Ile Asn Thr Gly Leu Cys Thr
                260                 265

<210> SEQ ID NO 2
<211> LENGTH: 363
<212> TYPE: PRT
<213> ORGANISM: Rhizomucor miehei

<400> SEQUENCE: 2

Met Val Leu Lys Gln Arg Ala Asn Tyr Leu Gly Phe Leu Ile Val Phe
                -90                 -85                 -80

Phe Thr Ala Phe Leu Val Glu Ala Val Pro Ile Lys Arg Gln Ser Asn
            -75                 -70                 -65

Ser Thr Val Asp Ser Leu Pro Pro Leu Ile Pro Ser Arg Thr Ser Ala
        -60                 -55                 -50

Pro Ser Ser Ser Pro Ser Thr Thr Asp Pro Glu Ala Pro Ala Met Ser
    -45                 -40                 -35

Arg Asn Gly Pro Leu Pro Ser Asp Val Glu Thr Lys Tyr Gly Met Ala
-30                 -25                 -20                 -15

Leu Asn Ala Thr Ser Tyr Pro Asp Ser Val Val Gln Ala Met Ser Ile
            -10                 -5                  -1   1

Asp Gly Gly Ile Arg Ala Ala Thr Ser Gln Glu Ile Asn Glu Leu Thr
        5                   10                  15

Tyr Tyr Thr Thr Leu Ser Ala Asn Ser Tyr Cys Arg Thr Val Ile Pro
    20                  25                  30

Gly Ala Thr Trp Asp Cys Ile His Cys Asp Ala Thr Glu Asp Leu Lys
35                  40                  45                  50

Ile Ile Lys Thr Trp Ser Thr Leu Ile Tyr Asp Thr Asn Ala Met Val
            55                  60                  65

Ala Arg Gly Asp Ser Glu Lys Thr Ile Tyr Ile Val Phe Arg Gly Ser
        70                  75                  80

Ser Ser Ile Arg Asn Trp Ile Ala Asp Leu Thr Phe Val Pro Val Ser
    85                  90                  95

Tyr Pro Pro Val Ser Gly Thr Lys Val His Lys Gly Phe Leu Asp Ser
100                 105                 110

Tyr Gly Glu Val Gln Asn Glu Leu Val Ala Thr Val Leu Asp Gln Phe
115                 120                 125                 130

Lys Gln Tyr Pro Ser Tyr Lys Val Ala Val Thr Gly His Ser Leu Gly
```

```
            135                 140                 145
Gly Ala Thr Ala Leu Leu Cys Ala Leu Asp Leu Tyr Gln Arg Glu Glu
            150                 155                 160

Gly Leu Ser Ser Asn Leu Phe Leu Tyr Thr Gln Gly Gln Pro Arg
            165                 170                 175

Val Gly Asp Pro Ala Phe Ala Asn Tyr Val Val Ser Thr Gly Ile Pro
            180                 185                 190

Tyr Arg Arg Thr Val Asn Glu Arg Asp Ile Val Pro His Leu Pro Pro
195                 200                 205                 210

Ala Ala Phe Gly Phe Leu His Ala Gly Glu Glu Tyr Trp Ile Thr Asp
            215                 220                 225

Asn Ser Pro Glu Thr Val Gln Val Cys Thr Ser Asp Leu Glu Thr Ser
            230                 235                 240

Asp Cys Ser Asn Ser Ile Val Pro Phe Thr Ser Val Leu Asp His Leu
            245                 250                 255

Ser Tyr Phe Gly Ile Asn Thr Gly Leu Cys Thr
            260                 265
```

<210> SEQ ID NO 3
<211> LENGTH: 269
<212> TYPE: PRT
<213> ORGANISM: Rhizomucor miehei

<400> SEQUENCE: 3

```
Ser Ile Asp Gly Gly Ile Arg Ala Ala Thr Ser Gln Glu Ile Asn Glu
1               5                   10                  15

Leu Thr Tyr Tyr Thr Thr Leu Ser Ala Asn Ser Tyr Cys Arg Thr Val
                20                  25                  30

Ile Pro Gly Ala Thr Trp Asp Cys Ile His Cys Asp Ala Thr Glu Asp
            35                  40                  45

Leu Lys Ile Ile Lys Thr Trp Ser Thr Leu Ile Tyr Asp Thr Asn Ala
        50                  55                  60

Met Val Ala Arg Gly Asp Ser Glu Lys Thr Ile Tyr Ile Val Phe Arg
65                  70                  75                  80

Gly Ser Ser Ser Ile Arg Asn Trp Ile Ala Asp Leu Thr Phe Val Pro
                85                  90                  95

Val Ser Tyr Pro Pro Val Ser Gly Thr Lys Val His Lys Gly Phe Leu
            100                 105                 110

Asp Ser Tyr Gly Glu Val Gln Asn Glu Leu Val Ala Thr Val Leu Asp
        115                 120                 125

Gln Phe Lys Gln Tyr Pro Ser Tyr Lys Val Ala Val Thr Gly His Ser
130                 135                 140

Leu Gly Gly Ala Thr Ala Leu Leu Cys Ala Leu Asp Leu Tyr Gln Arg
145                 150                 155                 160

Glu Glu Gly Leu Ser Ser Asn Leu Phe Leu Tyr Thr Gln Gly Gln
                165                 170                 175

Pro Arg Val Gly Asp Pro Ala Phe Ala Asn Tyr Val Val Ser Thr Gly
            180                 185                 190

Ile Pro Tyr Arg Arg Thr Val Asn Glu Arg Asp Ile Val Pro His Leu
        195                 200                 205

Pro Pro Ala Ala Phe Gly Phe Leu His Ala Gly Glu Glu Tyr Trp Ile
210                 215                 220

Thr Asp Asn Ser Pro Glu Thr Val Gln Val Cys Thr Ser Asp Leu Glu
225                 230                 235                 240
```

```
Thr Ser Asp Cys Ser Asn Ser Ile Val Pro Phe Thr Ser Val Leu Asp
                245                 250                 255

His Leu Ser Tyr Phe Gly Ile Asn Thr Gly Leu Cys Thr
            260                 265

<210> SEQ ID NO 4
<211> LENGTH: 70
<212> TYPE: PRT
<213> ORGANISM: Rhizomucor miehei

<400> SEQUENCE: 4

Val Pro Ile Lys Arg Gln Ser Asn Ser Thr Val Asp Ser Leu Pro Pro
1               5                   10                  15

Leu Ile Pro Ser Arg Thr Ser Ala Pro Ser Ser Ser Pro Ser Thr Thr
            20                  25                  30

Asp Pro Glu Ala Pro Ala Met Ser Arg Asn Gly Pro Leu Pro Ser Asp
        35                  40                  45

Val Glu Thr Lys Tyr Gly Met Ala Leu Asn Ala Thr Ser Tyr Pro Asp
    50                  55                  60

Ser Val Val Gln Ala Met
65                  70

<210> SEQ ID NO 5
<211> LENGTH: 269
<212> TYPE: PRT
<213> ORGANISM: Thermomyces lanuginosus

<400> SEQUENCE: 5

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
            35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
            115                 120                 125

Glu Asp Ala Val Arg Glu His Pro Asp Tyr Arg Val Val Phe Thr Gly
        130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220
```

```
Gly Thr Leu Val Pro Val Arg Arg Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265
```

<210> SEQ ID NO 6
<211> LENGTH: 384
<212> TYPE: PRT
<213> ORGANISM: Mucor circinelloides

<400> SEQUENCE: 6

```
Met Val Ser Phe Val Ser Ile Ser Gln Gly Ile Ser Leu Phe Ile Val
1               5                   10                  15

Val Ser Ser Met Leu Thr Gly Ser Ala His Ala Ala Pro Ala Ser Ser
                20                  25                  30

His Ser Asn Ser Ser Lys Asn Ala Thr Thr Ser Asp Ala Ser Thr Phe
            35                  40                  45

Thr Leu Pro Pro Ile Ile Ser Ser Arg Val Thr Pro Pro Lys Val Pro
50                  55                  60

Ser Gly Ser His Asn Val Glu Asp Ala Asn Val Ala Lys Asn Lys Lys
65                  70                  75                  80

Trp Phe Glu Ala His Gly Gly Lys Leu Asn Val Thr Lys Arg Ala Asp
                85                  90                  95

Glu Thr Val Gly Gly Tyr Thr Met Asp Leu Pro Ser Asn Ala Pro Pro
            100                 105                 110

Leu Pro Ala Val Pro Ser Thr Ser Val Val Ile Ala Ser Thr Ala
        115                 120                 125

Gln Ile Ser Glu Phe Lys Lys Tyr Ala Gly Ile Ala Ser Thr Ala Tyr
130                 135                 140

Cys Arg Ser Val Val Pro Leu Asn Gln Trp Ser Cys Thr Asn Cys Leu
145                 150                 155                 160

Lys Phe Val Pro Asp Gly Lys Leu Ile Lys Thr Phe Thr Ser Leu Val
                165                 170                 175

Thr Asp Thr Asn Gly Phe Val Leu Arg Ser Asp Ala Gln Lys Thr Ile
            180                 185                 190

Tyr Val Val Phe Arg Gly Thr Asn Ser Ile Arg Ser Ala Ile Thr Asp
        195                 200                 205

Leu Val Phe Glu Leu Thr Asn Tyr Thr Pro Val Ser Gly Ala Lys Val
210                 215                 220

His Thr Gly Phe Tyr Ala Ser Tyr Lys Ala Val Val Ser Asp Tyr Phe
225                 230                 235                 240

Pro Ala Val Gln Ser Gln Leu Thr Ala Tyr Pro Gly Tyr Lys Val Ile
                245                 250                 255

Val Thr Gly His Ser Leu Gly Gly Ala Gln Ala Leu Leu Ala Gly Met
            260                 265                 270

Asp Leu Tyr Gln Arg Glu Pro Arg Leu Ser Lys Ser Asn Leu Ala Ile
        275                 280                 285

Tyr Thr Val Gly Cys Pro Arg Val Gly Asn Pro Ala Phe Ala Tyr Tyr
290                 295                 300

Val Asp Ser Thr Gly Ile Thr Phe Ser Arg Ser Val Asn Asn Arg Asp
305                 310                 315                 320

Ile Val Pro His Val Pro Pro Gln Ala Trp Gly Phe Leu His Pro Gly
                325                 330                 335
```

Val Glu Ala Trp Ala Arg Ser Ser Asn Val Gln Ile Cys Thr Pro
            340                 345                 350

Asn Ile Glu Thr Gly Leu Cys Ser Asn Ser Ile Val Pro Phe Thr Ser
            355                 360                 365

Phe Thr Asp His Leu Thr Tyr Tyr Asp Leu Asn Glu Gly Leu Cys Leu
    370                 375                 380

<210> SEQ ID NO 7
<211> LENGTH: 389
<212> TYPE: PRT
<213> ORGANISM: Rhizopus microsporus var. chinensis

<400> SEQUENCE: 7

Met Val Ser Phe Ile Ser Ile Ser Gln Gly Val Ser Leu Cys Leu Leu
1               5                   10                  15

Val Ser Ser Met Met Leu Gly Ser Ser Ala Val Pro Val Ala Gly His
                20                  25                  30

Lys Gly Ser Val Lys Ala Thr Asn Gly Thr Asp Phe Gln Leu Pro Pro
            35                  40                  45

Leu Ile Ser Ser Arg Cys Thr Pro Pro Ser His Pro Glu Thr Thr Gly
    50                  55                  60

Asp Pro Asp Ala Glu Ala Tyr Tyr Ile Asn Lys Ser Val Gln Trp Tyr
65                  70                  75                  80

Gln Ala His Gly Gly Asn Tyr Thr Ala Leu Ile Lys Arg Asp Thr Glu
                85                  90                  95

Thr Val Gly Gly Met Thr Leu Asp Leu Pro Glu Asn Pro Pro Pro Ile
            100                 105                 110

Pro Ala Thr Ser Thr Ala Pro Ser Ser Asp Ser Gly Glu Val Val Thr
        115                 120                 125

Ala Thr Ala Ala Gln Ile Lys Glu Leu Thr Asn Tyr Ala Gly Val Ala
130                 135                 140

Ala Thr Ala Tyr Cys Arg Ser Val Val Pro Gly Thr Lys Trp Asp Cys
145                 150                 155                 160

Lys Gln Cys Leu Lys Tyr Val Pro Asp Gly Lys Leu Ile Lys Thr Phe
                165                 170                 175

Thr Ser Leu Leu Thr Asp Thr Asn Gly Phe Ile Leu Arg Ser Asp Ala
            180                 185                 190

Gln Lys Thr Ile Tyr Val Thr Phe Arg Gly Thr Asn Ser Phe Arg Ser
        195                 200                 205

Ala Ile Thr Asp Met Val Phe Thr Phe Thr Asp Tyr Ser Pro Val Lys
210                 215                 220

Gly Ala Lys Val His Ala Gly Phe Leu Ser Ser Tyr Asn Gln Val Val
225                 230                 235                 240

Lys Asp Tyr Phe Pro Val Val Gln Asp Gln Leu Thr Ala Tyr Pro Asp
                245                 250                 255

Tyr Lys Val Ile Val Thr Gly His Ser Leu Gly Gly Ala Gln Ala Leu
            260                 265                 270

Leu Ala Gly Met Asp Leu Tyr Gln Arg Glu Lys Arg Leu Ser Pro Lys
        275                 280                 285

Asn Leu Ser Ile Tyr Thr Val Gly Cys Pro Arg Val Gly Asn Asn Ala
290                 295                 300

Phe Ala Tyr Tyr Val Asp Ser Thr Gly Ile Pro Phe His Arg Thr Val
305                 310                 315                 320

His Lys Arg Asp Ile Val Pro His Val Pro Pro Gln Ala Phe Gly Tyr

```
                    325                 330                 335
Leu His Pro Gly Val Glu Ser Trp Ile Lys Glu Asp Pro Ala Asp Val
                340                 345                 350

Gln Ile Cys Thr Ser Asn Ile Glu Thr Lys Gln Cys Ser Asn Ser Ile
            355                 360                 365

Val Pro Phe Thr Ser Ile Ala Asp His Leu Thr Tyr Phe Gly Ile Asn
    370                 375                 380

Glu Gly Ser Cys Leu
385

<210> SEQ ID NO 8
<211> LENGTH: 392
<212> TYPE: PRT
<213> ORGANISM: Rhizopus oryzae

<400> SEQUENCE: 8

Met Val Ser Phe Ile Ser Ile Ser Gln Gly Val Ser Leu Cys Leu Leu
1               5                   10                  15

Val Ser Ser Met Met Leu Gly Ser Ser Ala Val Pro Val Ser Gly Lys
            20                  25                  30

Ser Gly Ser Ser Asn Thr Ala Val Ser Ala Ser Asp Asn Ala Ala Leu
        35                  40                  45

Pro Pro Leu Ile Ser Ser Arg Cys Ala Pro Ser Asn Lys Gly Ser
    50                  55                  60

Lys Ser Asp Leu Gln Ala Glu Pro Tyr Asn Met Gln Lys Asn Thr Glu
65                  70                  75                  80

Trp Tyr Glu Ser His Gly Gly Asn Leu Thr Ser Ile Gly Lys Arg Asp
                85                  90                  95

Asp Asn Leu Val Gly Gly Met Thr Leu Asp Leu Pro Ser Asp Ala Pro
            100                 105                 110

Pro Ile Ser Leu Ser Ser Thr Asn Ser Ala Ser Asp Gly Gly Lys
        115                 120                 125

Val Val Ala Ala Thr Thr Ala Gln Ile Gln Glu Phe Thr Lys Tyr Ala
    130                 135                 140

Gly Ile Ala Ala Thr Ala Tyr Cys Arg Ser Val Val Pro Gly Asn Lys
145                 150                 155                 160

Trp Asp Cys Val Gln Cys Gln Lys Trp Val Pro Asp Gly Lys Ile Ile
                165                 170                 175

Thr Thr Phe Thr Ser Leu Leu Ser Asp Thr Asn Gly Tyr Val Leu Arg
            180                 185                 190

Ser Asp Lys Gln Lys Thr Ile Tyr Leu Val Phe Arg Gly Thr Asn Ser
        195                 200                 205

Phe Arg Ser Ala Ile Thr Asp Ile Val Phe Asn Phe Ser Asp Tyr Lys
    210                 215                 220

Pro Val Lys Gly Ala Lys Val His Ala Gly Phe Leu Ser Ser Tyr Glu
225                 230                 235                 240

Gln Val Val Asn Asp Tyr Phe Pro Val Val Gln Glu Gln Leu Thr Ala
                245                 250                 255

His Pro Thr Tyr Lys Val Ile Val Thr Gly His Ser Leu Gly Gly Ala
            260                 265                 270

Gln Ala Leu Leu Ala Gly Met Asp Leu Tyr Gln Arg Glu Pro Arg Leu
        275                 280                 285

Ser Pro Lys Asn Leu Ser Ile Phe Thr Val Gly Gly Pro Arg Val Gly
    290                 295                 300
```

```
-continued

Asn Pro Thr Phe Ala Tyr Tyr Val Glu Ser Thr Gly Ile Pro Phe Gln
305                 310             315             320

Arg Thr Val His Lys Arg Asp Ile Val Pro His Val Pro Pro Gln Ser
                325             330             335

Phe Gly Phe Leu His Pro Gly Val Glu Ser Trp Ile Lys Ser Gly Thr
            340             345             350

Ser Asn Val Gln Ile Cys Thr Ser Glu Ile Glu Thr Lys Asp Cys Ser
        355             360             365

Asn Ser Ile Val Pro Phe Thr Ser Ile Leu Asp His Leu Ser Tyr Phe
    370             375             380

Asp Ile Asn Glu Gly Ser Cys Leu
385             390
```